(12) United States Patent
Rhodes et al.

(10) Patent No.: US 11,583,403 B2
(45) Date of Patent: Feb. 21, 2023

(54) BONE IMPLANT HOLDING AND SHAPING TRAY

(71) Applicant: Warsaw Orthopedic, Inc., Warsaw, IN (US)

(72) Inventors: Cheyenne S. Rhodes, Memphis, TN (US); Daniel A. Shimko, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 210 days.

(21) Appl. No.: 17/005,375

(22) Filed: Aug. 28, 2020

(65) Prior Publication Data

US 2021/0145588 A1    May 20, 2021

Related U.S. Application Data

(60) Provisional application No. 62/935,934, filed on Nov. 15, 2019.

(51) Int. Cl.
| | |
|---|---|
| *A61F 2/30* | (2006.01) |
| *A61B 50/33* | (2016.01) |
| *A61F 2/46* | (2006.01) |
| *A61F 2/28* | (2006.01) |
| *A61F 2/00* | (2006.01) |

(52) U.S. Cl.
CPC ............ *A61F 2/2846* (2013.01); *A61B 50/33* (2016.02); *A61F 2/0095* (2013.01); *A61F 2/3094* (2013.01); *A61F 2/30907* (2013.01); *A61F 2/4644* (2013.01); *A61F 2002/305* (2013.01); *A61F 2002/30112* (2013.01); *A61F 2002/30154* (2013.01); *A61F 2002/30158* (2013.01); *A61F 2002/30164* (2013.01)

(58) Field of Classification Search
CPC ............................ A61F 2/4644; A61F 2/0095
See application file for complete search history.

(56) References Cited

U.S. PATENT DOCUMENTS

| | | | |
|---|---|---|---|
| 3,255,570 A | 6/1966 | Weimer | |
| 5,433,256 A | 7/1995 | Vasers | |
| 5,588,745 A | 12/1996 | Tanaka et al. | |
| 5,669,501 A * | 9/1997 | Hissong | A61B 50/33 206/363 |
| 6,196,426 B1 | 3/2001 | White | |

(Continued)

FOREIGN PATENT DOCUMENTS

| | | |
|---|---|---|
| CN | 204779918 | 11/2015 |
| WO | 2015/132034 | 9/2015 |

(Continued)

*Primary Examiner* — Javier G Blanco
(74) *Attorney, Agent, or Firm* — Sorell, Lenna & Schmidt, LLP

(57) ABSTRACT

A bone implant holding and shaping tray is provided. The tray includes a first segment having a distal end and a first surface sized to hold and shape at least a portion of the bone implant with bone material. The tray includes a second segment having a second surface sized to hold and shape at least a portion of the bone implant with bone material, the second segment having a proximal end configured to be coupled to the distal end of the first segment so as to extend the first surface to hold and shape the bone implant. Methods of making and using the bone implant holding and shaping tray are also provided.

10 Claims, 20 Drawing Sheets

(56) References Cited

U.S. PATENT DOCUMENTS

| | | | |
|---|---|---|---|
| 6,364,519 B1 | 4/2002 | Hughes et al. | |
| 6,582,438 B2 | 6/2003 | DeMayo | |
| 8,685,031 B2 | 4/2014 | Kleiner et al. | |
| 8,795,365 B2 | 8/2014 | Arcenio et al. | |
| 8,900,620 B2 | 12/2014 | Fulmer et al. | |
| 9,033,994 B2 | 5/2015 | Fingerhut | |
| 9,101,475 B2 | 8/2015 | Wei et al. | |
| 9,101,606 B2 | 8/2015 | Drapeau et al. | |
| 9,220,598 B2 | 12/2015 | Betz et al. | |
| 9,333,082 B2 | 5/2016 | Wei et al. | |
| 9,394,152 B2 | 7/2016 | Connellan et al. | |
| 9,492,278 B2 | 11/2016 | Wei et al. | |
| 10,349,994 B1* | 7/2019 | Elgafy | A61F 2/4601 |
| 2002/0112981 A1* | 8/2002 | Cooper | A61B 90/94 |
| | | | 206/570 |
| 2005/0155901 A1 | 7/2005 | Kreuger et al. | |
| 2007/0269475 A1* | 11/2007 | Gil | A61F 2/4644 |
| | | | 424/422 |
| 2009/0234452 A1* | 9/2009 | Steiner | A61F 2/4644 |
| | | | 623/14.12 |
| 2010/0179507 A1 | 7/2010 | Hess et al. | |
| 2011/0015640 A1 | 1/2011 | Hess et al. | |
| 2011/0054408 A1 | 3/2011 | Wei et al. | |
| 2011/0060227 A1 | 3/2011 | Saadat | |
| 2011/0140316 A1* | 6/2011 | Bagga | A61F 2/28 |
| | | | 264/319 |
| 2012/0065613 A1 | 3/2012 | Pepper et al. | |
| 2014/0263389 A1 | 9/2014 | Perozek et al. | |
| 2016/0038207 A1 | 2/2016 | Wei et al. | |
| 2016/0250038 A1 | 9/2016 | Wei et al. | |
| 2018/0250145 A1 | 9/2018 | Stevenson et al. | |

FOREIGN PATENT DOCUMENTS

| | | | | |
|---|---|---|---|---|
| WO | WO-2015132034 A1 * | 9/2015 | | A61B 17/8816 |
| WO | WO-2015160348 A1 * | 10/2015 | | A61B 50/00 |
| WO | 2019/040851 | 2/2019 | | |
| WO | WO-2019104122 A1 * | 5/2019 | | A61B 50/30 |
| WO | WO-2021011821 A1 * | 1/2021 | | A01N 1/0273 |

* cited by examiner

BONE IMPLANT HOLDING AND SHAPING TRAY

CROSS-REFERENCE TO RELATED APPLICATION

This application claims the benefit of and priority to U.S. Provisional Patent Application No. 62/935,934 filed Nov. 15, 2019, the entire disclosure of which is incorporated by reference herein.

BACKGROUND

The use of bone grafts and bone substitute materials in orthopedic medicine is known. While bone wounds can regenerate without the formation of scar tissue, fractures and other orthopedic injuries take a long time to heal, during which time the bone is unable to support physiologic loading unaided. Metal pins, screws, rods, plates and meshes are frequently required to replace the mechanical functions of injured bone. However, metal is significantly stiffer than bone. Use of metal implants may result in decreased bone density around the implant site due to stress shielding. Physiologic stresses and corrosion may cause metal implants to fracture. Unlike bone, which can heal small damage cracks through remodeling to prevent more extensive damage and failure, damaged metal implants can only be replaced or removed. The natural cellular healing and remodeling mechanisms of the body coordinate removal of bone and bone grafts by osteoclast cells and formation of bone by osteoblast cells.

Conventionally, bone tissue regeneration is achieved by treating a bone repair site with a bone graft. Over time, the bone graft is incorporated by the host and new bone remodels the bone graft. In order to place the bone graft, it is common to use a monolithic bone pre-formed graft or to form an osteoimplant comprising particulated bone in a carrier. Generally, the formed implant, whether monolithic or particulated and in a carrier is substantially solid at the time of implantation and thus does not conform to the implant site. The implant is also substantially complete at the time of implantation and thus provides little ability for customization, for example by the addition of autograft or alteration of the shape of the implant.

The use of bone grafts is generally limited by the available shape and size of grafts. Further, bone grafts using cortical bone remodel slowly because of their limited porosity. Traditional bone substitute materials are more quickly remodeled but cannot immediately provide mechanical support. In addition, while bone substitute materials can be used to fill and/or treat oddly shaped bone defects by themselves, such materials are not as well suited for wrapping or resurfacing bone.

Moreover, in operating rooms the size of an aseptic, sterile environment is frequently limited. Bone grafting kits used by surgeons to place a bone graft often include disposable instruments. These need to be packaged in sterile barriers. If the kits are too big, they will not fit well on hospital shelves. Because of their size, large instruments can cause problems in surgery as they take up extra space and have a large footprint storage in the sterile field.

Therefore, it would be beneficial and desirable to provide bone implants that can be shaped with bone material (e.g., natural bone particles and/or synthetic bone particles) on a forming tray that can vary in length but is stackable or nestable into a small footprint storage area but slidable or unnested to open into a longer and larger tray during surgery.

SUMMARY

Trays are provided that allow bone implants to be shaped with bone material (e.g., natural bone particles and/or synthetic bone particles), where the tray can vary in length. These trays enable surgeons to reproducibly shape bone implants to a size determined at the time of surgery. The trays can facilitate filling and/or wrapping of bone materials into or with biocompatible containment devices such as resorbable polymer mesh. In some embodiments, the tray can be stackable or nestable into a smaller storage configuration but slidable or unnested to a larger configuration when the implant is shaped.

A bone implant holding and shaping tray is provided. The tray includes a first segment having a distal end, and a first surface sized to hold and shape at least a portion of the bone implant with bone material. The tray also includes a second segment having a second surface sized to hold and shape at least a portion of the bone implant with bone material, the second segment having a proximal end configured to be coupled to the distal end of the first segment so as to extend the first surface to hold and shape the bone implant.

In another embodiment, the tray comprises a first segment having a bottom surface, and a first surface sized to hold and shape at least a portion of the bone implant with bone material. In this embodiment, the tray also comprises a second segment having a second surface sized to hold and shape at least a portion of the bone implant with bone material, the second segment having a top surface configured to be coupled to the bottom surface of the first segment so as to extend the first surface to hold and shape the bone implant.

A method of making a bone implant holding and shaping tray is provided. The method includes providing a first segment having a distal end, and a first surface sized to hold and shape at least a portion of the bone implant with bone material. The method also includes providing a second segment having a second surface sized to hold and shape at least a portion of the bone implant with bone material, the second segment having a proximal end configured to be coupled to the distal end of the first segment. The method further includes coupling the distal end of the first segment with the proximal end of the second segment so as to extend the first surface to form the tray for holding and shaping the bone implant.

In another embodiment, the method of making a bone implant holding and shaping tray includes providing a first segment having a bottom surface, and a first surface sized to hold and shape at least a portion of the bone implant with bone material. The method also includes providing a second segment having a second surface sized to hold and shape at least a portion of the bone implant with bone material, the second segment having top surface configured to be coupled to the bottom surface of the first segment and coupling the bottom surface of the first segment to the top surface of the second segment so as to extend the bottom surface of the first segment to form the tray for holding and shaping the bone implant.

A method of shaping bone material into a bone implant is also provided. In certain embodiments, the method comprises providing a tray having a first segment having a distal end, and a first surface sized to hold and shape at least a portion of the bone implant with bone material; and the tray comprising a second segment having a second surface sized to hold and shape at least a portion of the bone implant with bone material, the second segment having a proximal end configured to be coupled to the distal end of the first segment so as to extend the first surface to hold and shape the bone implant; providing the bone implant comprising a mesh having an inner surface and an outer surface opposing the inner surface, the inner surface configured to receive the bone material when the inner surface is in the open configuration; disposing the bone material into the inner surface of the mesh by orienting the mesh in the open configuration; and enclosing the bone material in the mesh by orienting the mesh in the closed configuration.

In another embodiment, the method of shaping bone material into a bone implant includes providing a first segment having a bottom surface, and a first surface sized to hold and shape at least a portion of the bone implant with bone material; and the tray comprising a second segment having a second surface sized to hold and shape at least a portion of the bone implant with bone material, the second segment having top surface configured to be coupled to the bottom surface of the first segment so as to extend the first surface to hold and shape the bone implant; providing the bone implant comprising a mesh having an inner surface and an outer surface opposing the inner surface, the inner surface configured to receive the bone material when the inner surface is in the open configuration; and disposing the bone material into the inner surface of the mesh by orienting the mesh in the open configuration; and enclosing the bone material in the mesh by orienting the mesh in the closed configuration.

In another embodiment, the method of shaping bone material into a bone implant includes placement and orientation of the mesh first within the tray in an open configuration followed by placement and shaping of the bone material within or onto the mesh after which the mesh is oriented to the closed configuration.

While multiple embodiments are disclosed, still other embodiments of the present disclosure will become apparent to those skilled in the art from the following detailed description. As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE FIGURES

In part, other aspects, features, benefits and advantages of the embodiments will be apparent with regard to the following description, appended claims and accompanying figures where:

Figure 1:
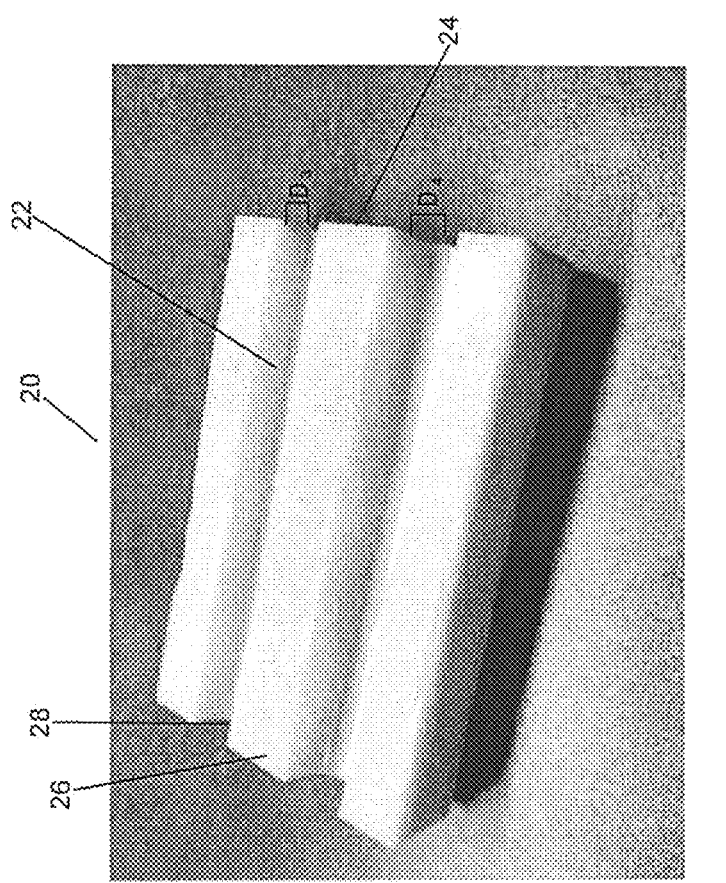
FIG. 1 depicts a perspective view of a first segment and second segment of an unassembled bone implant holding and shaping tray.
Figure 1:
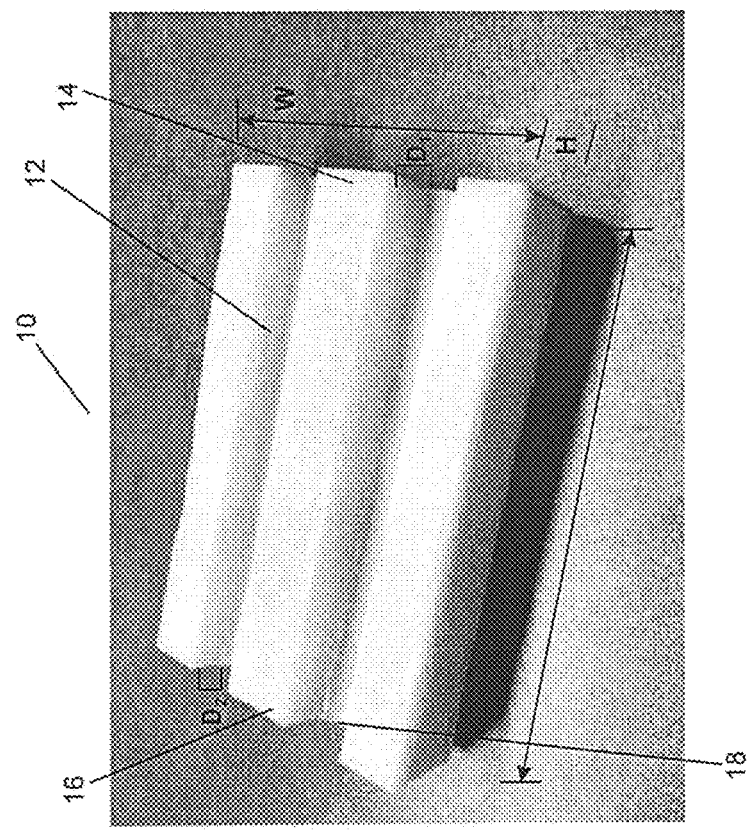

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

It is noted that, as used in this specification and the appended claims, the singular forms "a," "an," and "the," include plural referents unless expressly and unequivocally limited to one referent. For example, reference to "a container" includes one, two, three or more containers.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "xenograft" refers to tissue or organs from an individual of one species transplanted into or grafted onto an organism of another species, genus, or family.

The term "mammal" refers to organisms from the taxonomy class "mammalian," including, but not limited to, humans; other primates, such as chimpanzees, apes, orangutans and monkeys; rats, mice, cats, dogs, cows, horses, etc.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "bone material" includes natural and/or inorganic material such as, for example, inorganic ceramic and/or bone substitute material. The bone material can also include natural bone material such as, for example, bone which is cortical, cancellous or cortico-cancellous of autogenous, allogenic, xenogenic, or transgenic origin. In some embodiments, bone material can include demineralized bone material such as, for example, substantially demineralized bone material, partially demineralized bone material, or fully demineralized bone material.

"Demineralized" as used herein, refers to any material generated by removing mineral material from tissue, e.g., bone tissue. In certain embodiments, the demineralized compositions described herein include preparations containing less than 5% calcium and preferably less than 1% calcium by weight. Partially demineralized bone (e.g., preparations with greater than 5% calcium by weight but containing less than 100% of the original starting amount of calcium) is also considered within the scope of the application. In some embodiments, demineralized bone has less than 95% of its original mineral content.

In some embodiments, demineralized bone has less than 95% of its original mineral content. In some embodiments, demineralized bone has less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "demineralized" is intended to encompass such expressions as "substantially demineralized," "superficially demineralized," "partially demineralized," "surface demineralized," and "fully demineralized."

"Partially demineralized" is intended to encompass "surface demineralized." "Partially demineralized bone" is intended to refer to preparations with greater than 5% calcium by weight but containing less than 100% of the original starting amount of calcium. In some embodiments, partially demineralized comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

"Superficially demineralized" as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

"Demineralized bone matrix" as used herein, refers to any material generated by removing mineral material from bone tissue. In preferred embodiments, the DBM compositions as used herein include preparations containing less than 5% calcium and preferably less than 1% calcium by weight.

"Biocompatible" as used herein, refers to materials that, upon administration in vivo, do not induce undesirable long-term effects.

"Osteoconductive" as used herein, refers to the ability of a non-osteoinductive substance to serve as a suitable template or substance along which bone may grow.

"Osteogenic", as used herein, refers to the ability of an agent, material, or implant to enhance or accelerate the growth of new bone tissue by one or more mechanisms such as osteogenesis, osteoconduction, and/or osteoinduction.

"Osteoinductive" as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

"Shaped" as used herein, refers to giving form, shape, organization, or geometrical character to a material. In some embodiments, the implant can be filled either partially or completely with bone material, which will allow the implant to be shaped to the particular geometry of the bone defect.

The terms "upper", "lower", "top", "bottom", "side", "proximal", "distal" and so forth have been used herein merely for convenience to describe the present invention and its parts as oriented in the drawings. It is to be understood, however, that these terms are in no way limiting to the disclosure since the delivery systems described herein may obviously be disposed in different orientations when in use.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention is an approximation; the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the disclosure, examples of which are illustrated in the accompanying figures. While the disclosure will be described in conjunction with the illustrated embodiments, it will be understood that they are not intended to limit the disclosure to those embodiments. On the contrary, the disclosure is intended to cover all alternatives, modifications, and equivalents that may be included within the disclosure as defined by the appended claims.

The headings below are not meant to limit the disclosure in any way; embodiments under anyone heading may be used in conjunction with embodiments under any other heading.

Adjustable Trays

In some embodiments, there is a bone implant holding and shaping tray provided that has an extendable surface and an adjustable length. The tray comprises a first segment having a distal end, and a first surface sized to hold and shape at least a portion of the bone implant with bone material; and the tray also comprises a second segment having a second surface sized to hold and shape at least a portion of the bone implant with bone material, the second segment having a proximal end configured to be coupled to the distal end of the first segment so as to extend the first surface to hold and shape the bone implant.

In certain embodiments (i) the distal end of the first segment of the tray is slidably coupled to the proximal end of the second segment of the tray; or (ii) the proximal end of the second segment is slidably coupled to the distal end of the first segment of the tray; or (iii) a portion of the distal end of the first segment slides within the proximal end of the first segment of the tray or (iv) a portion of the proximal end of second segment slides within the distal end of the first segment of the tray. In other embodiments, the first segment of the tray comprises a plurality of segments, each segment configured to be slidably coupled to each other and then to the second segment. In yet other aspects, the tray comprises a third segment having a third surface sized to hold and shape at least a portion of the bone implant with bone material, the third segment having a proximal end configured to be coupled to a distal end of the second segment so as to extend the second surface to hold and shape the bone implant.

In various embodiments, the distal end of the first segment of the tray and the proximal end of the second segment of the tray are coupled by mating surfaces configured to lock the first segment with the second segment of the tray. In certain aspects, the mating surfaces comprise a snap fit fitting, an interference fitting or a tab-slot fitting. In other aspects, one of the mating surfaces is located at the distal end of the first segment of the tray and the other mating surface is located at the proximal end of the second segment of the tray. In various aspects, each mating surface is disposed all around a perimeter and/or the first surface of the first segment of the tray and/or a perimeter and/or the second surface of the second segment of the tray. In different embodiments, the mating surfaces can have a round, toothed, square, trapezoidal, dovetail, spiked or cantilever shaped, or a combination thereof.

In various embodiments, the first surface of the first segment and the second surface of the second segment comprise a plurality of markers extending from the distal end of each segment to a region adjacent to the proximal end of each segment, each of the plurality of markers spaced a distance apart from each other such that a measured amount of a bone material can be placed between markers for a measured dispensing of the bone material into a bone implant and/or to hold and shape the bone implant. In certain embodiments, the first surface of the first segment or the second surface of the second segment further comprises a mixing surface comprising a bowl configured to mix the bone material.

In some embodiments, the tray has a retracted configuration such that the first segment and the second segment are nested together and the first surface of the first segment covers the second surface of the second segment completely. In some embodiments, in the retracted configuration, the tray has a compact size, in which the first segment and the second segment are nested together and their top surfaces overlap with each other and the tray has the smallest dimension in this configuration. In some embodiments, the retracted configuration allows the first segment and the second segment to stack or overlap completely such that the proximal end of the first segment is above the distal end of the second segment and the distal end of the first segment is above the proximal end of the second segment. In some embodiments, the overlap may exist only on the surface such that an edge of the distal end of the second segment is not covered by the proximal end of the first segment. In some embodiments, the retracted configuration allows the tray to have a smaller footprint for storage.

In some embodiments, the tray has an expanded configuration such that the tray has a length extended from a length of the first surface to a length of the second surface. In some embodiments, the tray has infinite expanded configurations as the first segment can extend from the second segment, or vise versa at infinite positions by sliding, nesting or stacking. In some embodiments, the expanded configuration includes a maximized length of the tray.

In some embodiments, the distal end of the first surface of the first segment has an open end and the proximal end of the second surface has an open end, such that the first surface and the second surface have a seamless connection when the first segment and the second segment are coupled. In some embodiments, the seamless connection includes a seamless overlap along a length of the tray. In some embodiments, the first surface of the first segment overlaps the second surface of the second segment; while the overlapping length has no disruption or obstacles in vertical direction perpendicular to a longitudinal axis along the length of the tray. In some embodiments, the expanded configuration allows the tray to maximize the use of the first surface of the first segment and the second surface of the second segment.

In certain embodiments, there is provided a bone implant holding and shaping tray that can be extendable. The tray comprises a first segment having a bottom surface and a first surface sized to hold and shape at least a portion of the bone implant with bone material; and the tray comprises a second segment having a second surface sized to hold and shape at least a portion of the bone implant with bone material, the second segment having top surface configured to be coupled to the bottom surface of the first segment so as to extend the first surface to hold and shape the bone implant. In other embodiments, (i) the bottom surface of the first segment of the tray is stackable over the top surface of the second segment of the tray and/or (ii) the bottom surface of the first segment is slidable over the top surface of the second segment of the tray.

In some embodiments, the tray further comprises a third segment having a third surface sized to hold and shape at least a portion of the bone implant with bone material, the third segment having a top surface configured to be coupled to a bottom surface of the second segment of the tray so as to extend the second surface of the second segment of the tray to hold and shape the bone implant.

In many aspects, the bottom surface of the first segment of the tray is coupled to the top surface of the second segment of the tray by mating surfaces. In some aspects, one of the mating surfaces is disposed at a distal end of the bottom surface of the first segment of the tray and the other mating surface is disposed at the proximal end of the top surface of the second segment of the tray.

In various embodiments, the first surface of the first segment and the second surface of the second segment of the tray comprise a plurality of markers extending from the distal end of each segment to a region adjacent to the proximal end of each segment, each of the plurality of markers spaced a distance apart from each other such that a measured amount of a bone material can be placed between each marker for a measured dispensing of the bone material into a bone implant and/or to hold and shape the bone implant.

In some embodiments, the first surface of the first segment or the second surface of the second segment of the tray further comprises a mixing surface comprising a bowl configured to mix the bone material.

In various embodiments, there is provided a method of making a bone implant holding and shaping tray. The method comprises providing a first segment having a distal end, and a first surface sized to hold and shape at least a portion of the bone implant with bone material; providing a second segment having a second surface sized to hold and shape at least a portion of the bone implant with bone material, the second segment having a proximal end configured to be coupled to the distal end of the first segment; and coupling the distal end of the first segment with the proximal end of the second segment so as to extend the first surface to form the tray for holding and shaping the bone implant.

In other embodiments, another method of making a bone implant holding and shaping tray is provided, the method comprising: providing a first segment having a bottom surface, and a first surface sized to hold and shape at least a portion of the bone implant with bone material; providing a second segment having a second surface sized to hold and shape at least a portion of the bone implant with bone material, the second segment having top surface configured to be coupled to the bottom surface of the first segment; coupling the bottom surface of the first segment to the top surface of the second segment so as to extend the bottom surface of the first segment to form the tray for holding and shaping the bone implant.

Figure 2:
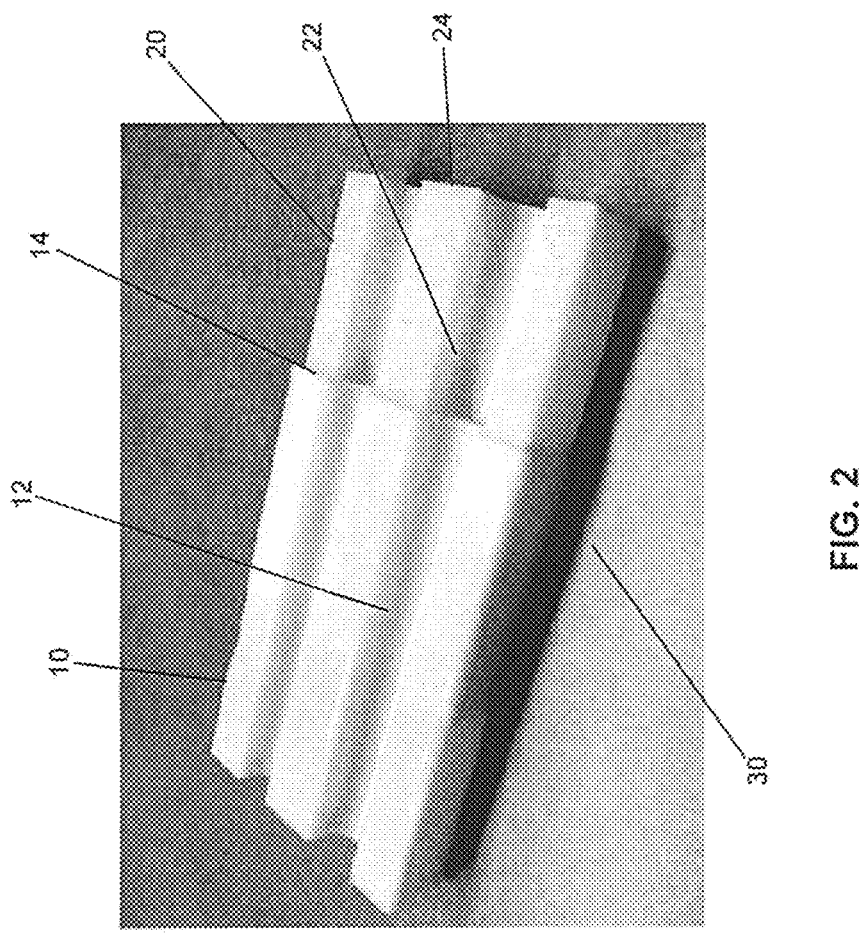
FIG. 2 depicts a perspective view of a slidably assembled bone implant holding and shaping tray.

FIGS. 1 and 2 are perspective views of a first segment 10 and a second segment 20 unassembled and slidably assembled as tray 30. First segment 10 has a first surface 12 sized to hold and shape at least a portion of a bone implant with bone material. First surface 12 has a distal end 14 and a proximal end 16. In some aspects, first segment 10 is solid at proximal end 16 and open at distal end 14. Distal end 14 is obtained by using a matched metal tool to cut so it is configured to match the contour of the second segment 20. In some aspects, first surface 12 can have the shape and configuration of a basic tray, namely square shaped. In other aspects, first surface 12 comprises a plurality of channels or wells 18 for holding bone implant, bone material and/or bone mesh. Channels 18 can have diameters of different sizes (e.g., D1, D2) and can comprise different profile shapes of variable geometry including, but not limited to, a square shape, rectangle shape, oval shape, and circle shape.

Figure 15A:
FIG. 15A is a diagram of a rounded rectangle shaped recess or channel in the first segment and/or the second segment of a bone implant holding and shaping tray.
Figure 15B:
FIG. 15B is a diagram of a partially rounded rectangle shaped recess or channel in the first segment and/or the second segment of a bone implant holding and shaping tray.
Figure 15C:
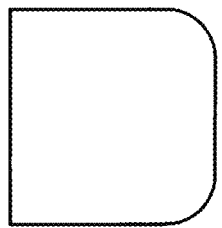
FIG. 15C is a diagram of a partially rounded square shaped recess or channel in the first segment and/or the second segment of a bone implant holding and shaping tray.
Figure 15D:
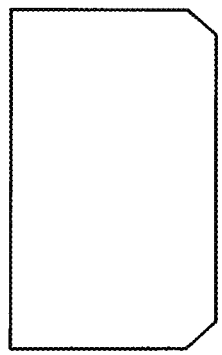
FIG. 15D is a diagram of a hexagonal shaped recess or channel in the first segment and/or the second segment of a bone implant holding and shaping tray.
Figure 15E:
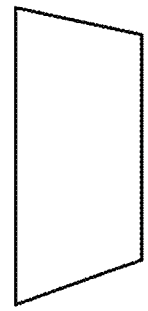
FIG. 15E is a diagram of a trapezoidal shaped recess or channel in the first segment and/or the second segment of a bone implant holding and shaping tray.
Figure 15F:
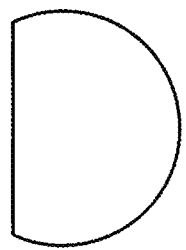
FIG. 15F is a diagram of a truncated circular shaped recess or channel in the first segment and/or the second segment of a bone implant holding and shaping tray.
Figure 15G:
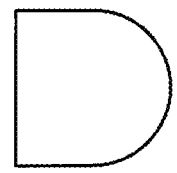
FIG. 15G is a diagram of a truncated rounded rectangle shaped recess or channel in the first segment and/or the second segment of a bone implant holding and shaping tray.
Figure 15H:
FIG. 15H is a diagram of a semicircular shaped recess or channel in the first segment and/or the second segment of a bone implant holding and shaping tray.
Figure 17A:
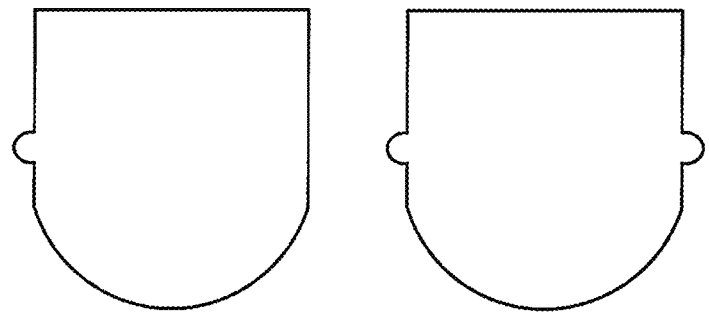
FIG. 17A is a side view of a recessed notch in the first segment and/or the second segment of a bone implant holding and shaping tray.
Figure 17B:
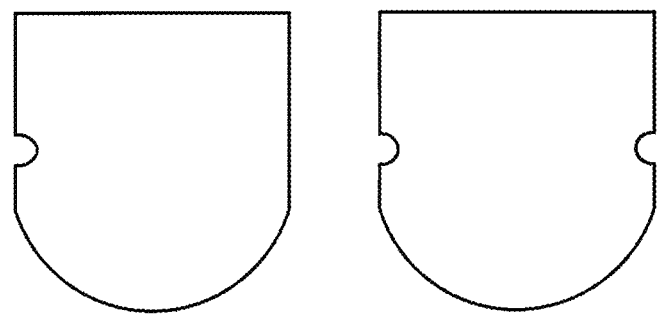
FIG. 17B is a side view of a raised notch in the first segment and/or the second segment of a bone implant holding and shaping tray.

Second segment 20 has a second surface 22 which is sized to hold and shape at least a portion of the bone implant with bone material. Second segment 20 also has a distal end 24 and a proximal end 26. Second surface 22, in some aspects, can have the shape and configuration of a basic tray, namely square shaped. In other aspects, second surface 22 comprises a plurality of recesses or depressions 28 for holding bone implant, bone material and/or bone mesh. Recesses or wells 28 can have diameters of different sizes (e.g., D3, D4) and can comprise different shapes of variable geometry including, but not limited to, a square shape, rectangle shape, oval shape, and circle shape. In some aspects, recess 28 can be a channel, a trough, slot, groove or grooves, an indent or indents or a combination thereof. In some embodiments, the diameter of each recess or channel can be from about 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, or 35 mm. In other aspects, recesses 28 can have various geometries are illustrated In FIGS. 15A to 15H. For example, these geometries include, without limitation, rounded rectangle (FIG. 15A), partially rounded rectangle (FIG. 15B), partially rounded square (FIG. 15C), hexagonal (FIG. 15D), trapezoidal (FIG. 15E), truncated circular (FIG. 15F), truncated rounded rectangle (FIG. 15G) and semicircular (FIG. 15H). In some embodiments, the recess or the well comprises a notch, running the length of the well, that denotes a lower fill quantity for the well. Having such notch in each well will increase the number of measured diameters on the tray without increasing the tray's overall footprint. In some embodiments, extra pre-determined diameter mark to denote smaller graft quantity fill-line, allowing a user to double number of diameters given on the tray without increasing the tray's overall footprint. In some embodiments, the notch comprises negative space, or a recessed notch, for example, as shown in FIG. 17A. In some embodiments, the notch comprises positive space, or a raised notch, for example, as shown in FIG. 17B.

In use, proximal end 26 of second segment 20 is configured to couple slidably to distal end 14 of first segment 10 so as to extend first surface 12 of first segment 10 to hold and shape the bone implant as illustrated in FIG. 2. First segment 10 and second segment 20 are illustrated assembled as tray 30 in FIG. 2.

Figure 3:
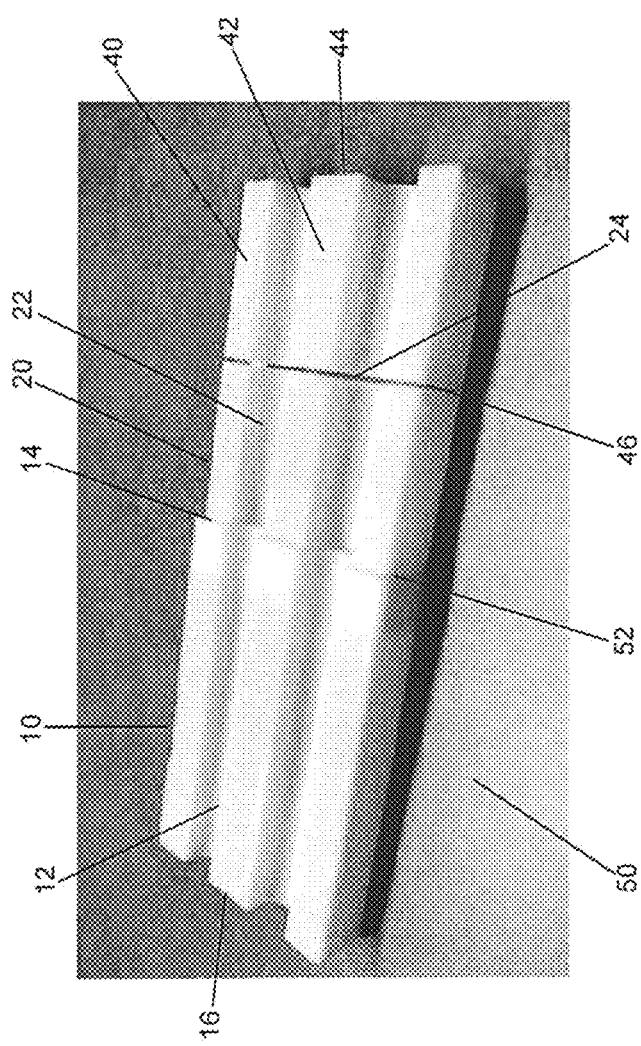
FIG. 3 depicts a perspective view of a slidably partially assembled bone implant holding and shaping tray, the tray being assembled from two of three segments.

FIG. 3 is a perspective view of tray 50 assembled from three distinct segments, first segment 10, second segment 20 and third segment 40. First segment 10 has first surface 12 disposed between proximal end 16 and distal end 14, second segment 20 has a second surface 22 disposed between proximal end 26 (shown in FIG. 1) and distal end 24 and third segment 40 has a third surface 42 disposed between proximal end 46 and distal end 44. In use, proximal end 46 of third segment 40 can slidably couple to distal end 24 of second segment 20 to form an extended, assembled tray 50. In some embodiments, the second segment and the third segment are monolithic and the second segment and the third segment are slidably coupled to the first segment to form an extended, assembled tray.

Each tray can have a selected length L shown in FIG. 1, such as, from about 2 inches to about 20 inches, from about 2 inches to about 15 inches, from about 2 inches to about 10 inches, from about 5 inches to about 20 inches, from about 5 inches to about 15 inches, from about 5 to about 10 inches, from about 10 inches to about 20 inches, from about 10 inches to about 20 inches, or from about 15 inches to about 20 inches. The length of the tray can be from about 1, 2, 3, 4, 5, 6, 7, 8, 9, 10, 11, 12, 13, 14, 15, 16, 17, 18, 19 or 20 inches.

The tray can have a selected width W shown in FIG. 1, such as, for example, from about 3 to about 12 inches, from about 3 to about 10 inches, from about 3 to about 8 inches, from about 3 to about 6 inches, from about 5 to about 12 inches, from about 5 to about 10 inches, from about 5 to about 8 inches, from about 8 to about 12 inches, or from about 8 to about 10 inches. The tray can have a width of about 1, 2, 3, 4, 5, 6, 7, 8, 9, 10, 11, or 12 inches.

The tray can have a selected height H shown in FIG. 1, when in a horizontal position, such as, for example, from about 0.25 inches to about 12 inches, from about 0.025 inches to about 10 inches, from about 0.25 inches to about 2 inches, from about 0.5 inches to about 12 inches, from about 0.5 inches to about 10 inches, or from about 0.5 inches to about 2 inches. The height of the tray can be from about 0.25, 0.5, 1, 2, 3, 4, 5, 6, 7, 8, 9, 10, 11, or 12 inches.

Figure 4:
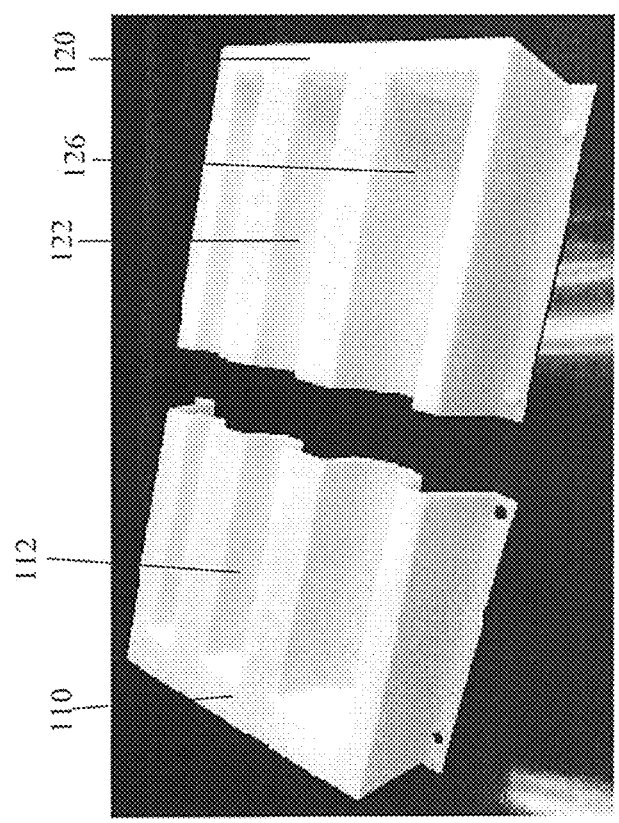
FIG. 4 depicts a perspective view of another embodiment of a first segment and a second segment of an unassembled bone implant holding and shaping tray.
Figure 5:
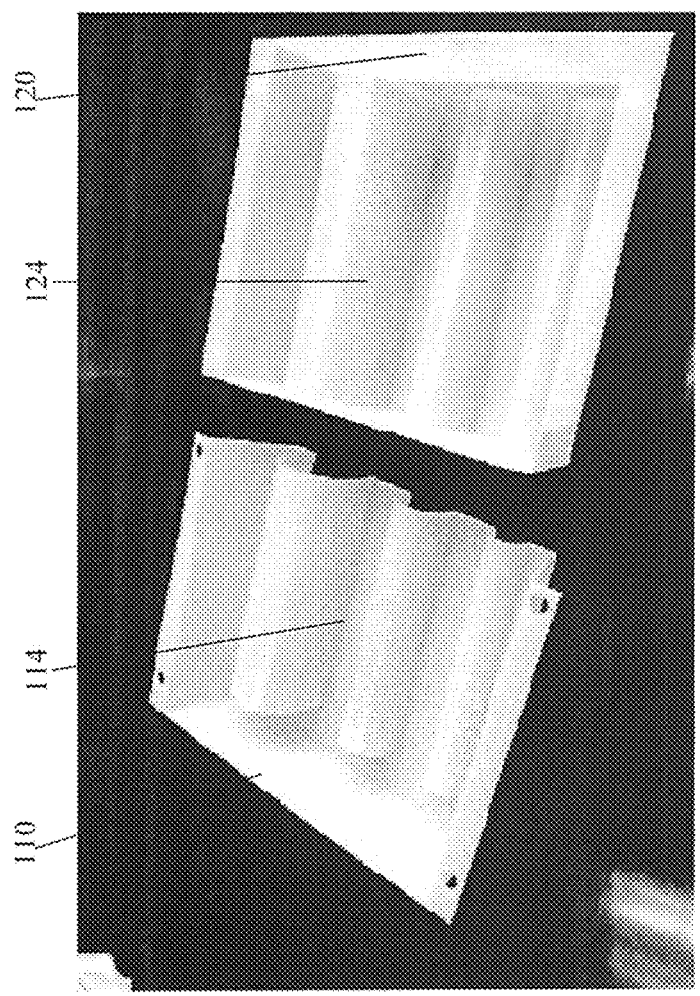
FIG. 5 depicts a perspective view of the bottom of a first segment and a second segment of an unassembled bone implant holding and shaping tray.

FIGS. 4-7 are perspective views of another embodiment of the trays of this disclosure. FIG. 4 illustrates a first segment 110 and a second segment 120, both unassembled. First segment 110 has a first surface 112 sized to hold and shape at least a portion of a bone implant with bone material and a bottom surface 114 shown in FIG. 5. Second segment 120 has a second surface 122 sized to hold and shape at least a portion of a bone implant with bone material. Second surface 122 has a bottom surface 124 and a top surface 126. In a stackable embodiment, top surface 126 of second segment 120 is configured to couple to the bottom surface 114 of first segment 110 so as to extend the first surface 112 to hold and to shape the bone implant. In some embodiments, the first segment comprises a side wall extending along a longitudinal axis between a proximal end and a distal end of the first segment. In some embodiments, the side wall comprises an edge surface extending away from the side wall along a horizontal axis perpendicular to the longitudinal axis. In some embodiments, the second segment comprises a second side wall extending along a longitudinal axis between a proximal end and a distal end of the second segment. In some embodiments, the side wall of the second segment comprises a second edge surface extending away from the side wall along a horizontal axis perpendicular to the longitudinal axis. In some embodiments, the edge surface comprises a depression, a cutout, a slot, or a hole such that they correspond to a protrusion, a pip, a notch or a cylindrical button and allow the first segment to couple with the second segment.

Figure 6:
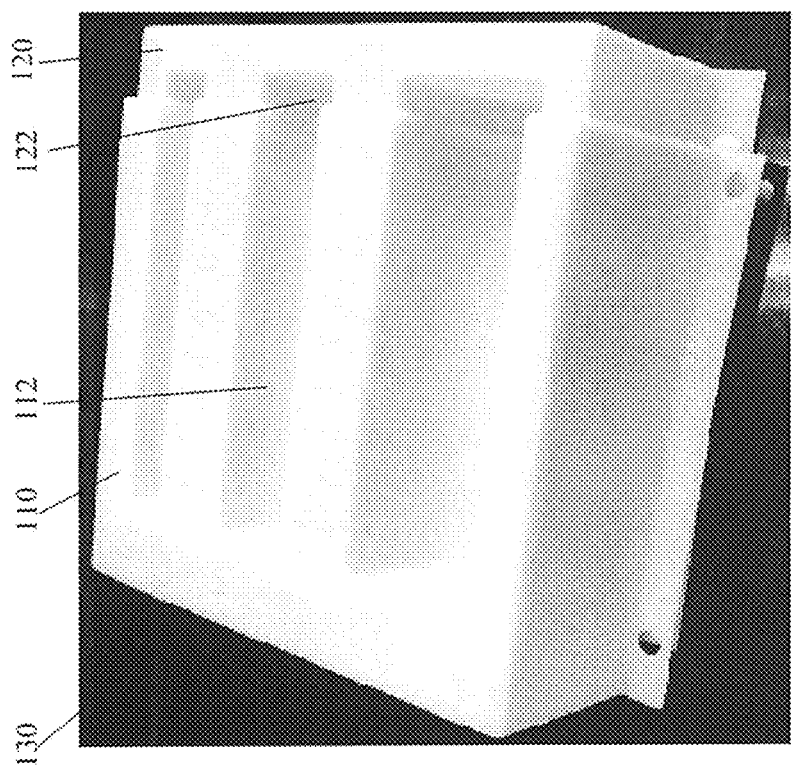
FIG. 6 depicts a perspective view of a stackable assembled bone implant holding and shaping tray in a retracted configuration.
Figure 7:
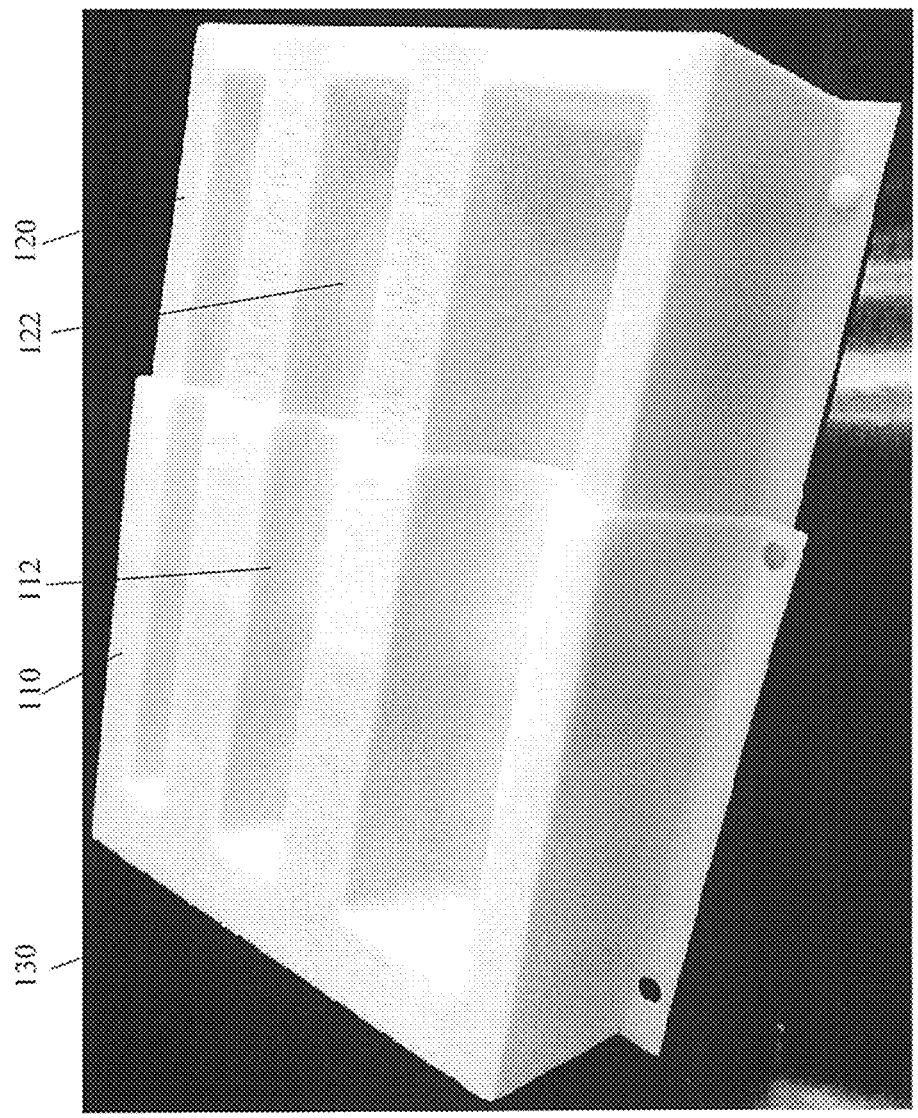
FIG. 7 depicts a perspective view of a stackable assembled bone implant holding and shaping tray in an expanded configuration.

In some embodiments, in a retracted configuration, the first segment and the second segment can be assembled to stack on one another as an assembled stackable tray 130, as illustrated in FIG. 6. This can be a compact configuration, which is a small footprint, that the tray can be packaged to save space and before use. In some embodiments, the top surface of the second segment is substantially covered by the bottom surface of the first segment. FIG. 7 illustrates an extended configuration, which has a fully stackable assembled tray 130 assembled from first segment 110 and second segment 120, where the top surface of the second segment is partially covered by the bottom surface of the first segment. This can be an extended configuration or not a compact configuration, which is a larger footprint, and can occur, in some embodiments, when the tray is unpacked and about to be used or is in use.

Figure 8:
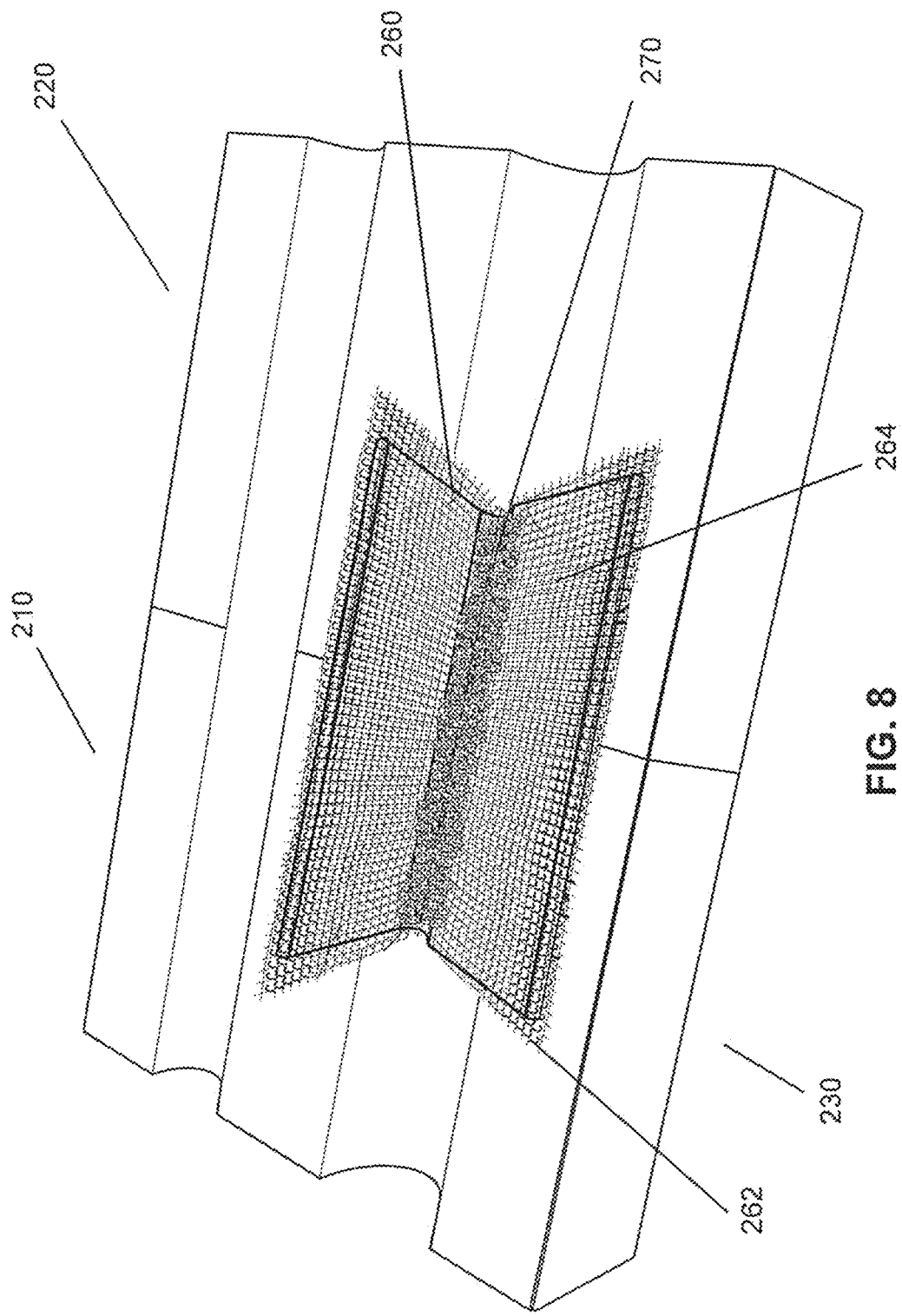
FIG. 8 depicts a perspective view of an assembled implant holding and shaping tray including a bone implant in an open configuration.
Figure 9A:
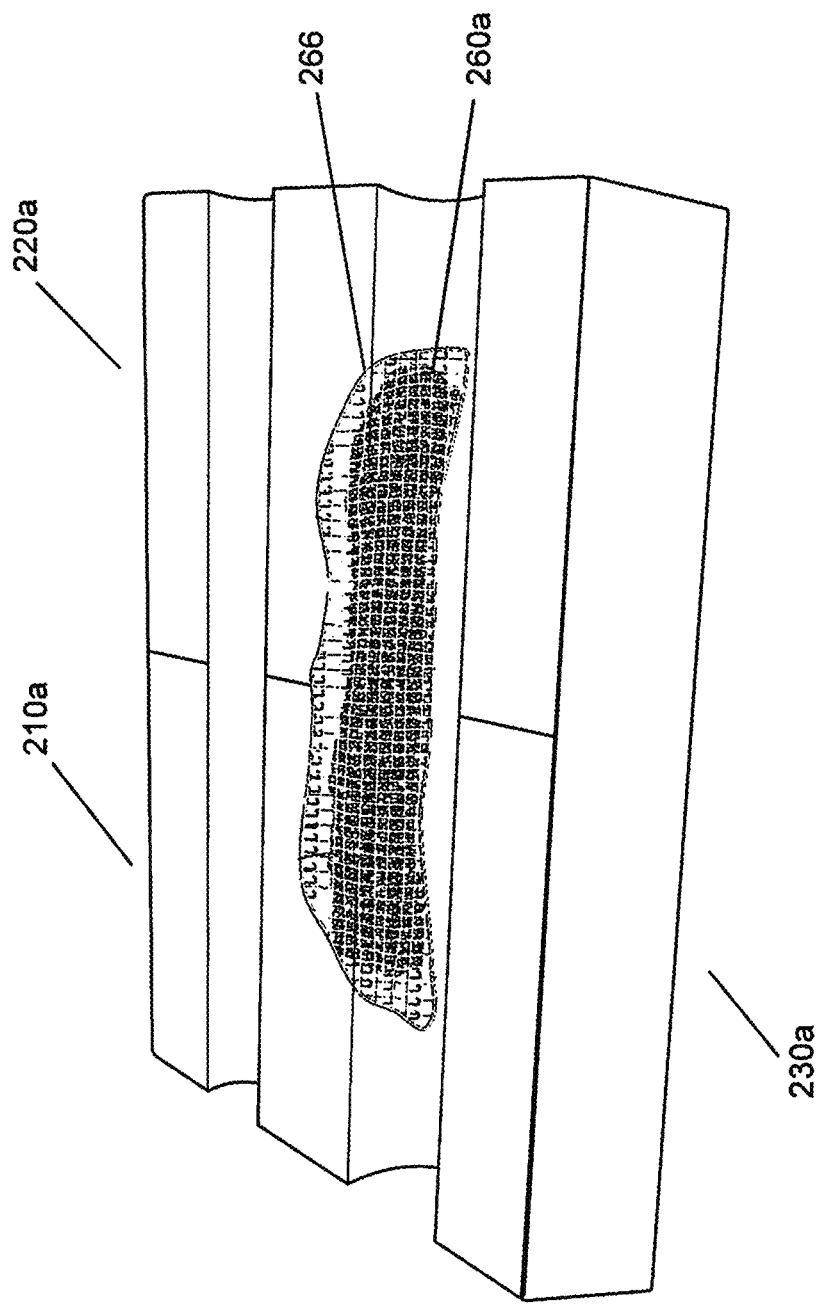
FIG. 9A depicts a perspective view of an assembled implant holding and shaping tray including a bone implant in a closed configuration.

FIG. 8 is a perspective view of a first segment 210 and second segment 220 of an assembled tray 230. Tray 230 comprises a bone implant 260 in an open configuration. Bone implant 260 comprises a mesh 262, an inner surface 264 and outer surface 266 illustrated in FIG. 9A. Bone implant 260 includes bone material 270. FIG. 9A illustrates a perspective view of a related embodiment wherein tray 230a is assembled slidably from first segment 210a and second segment 220a to hold bone implant 260a shaped with bone material in a closed configuration.

Figure 9B:
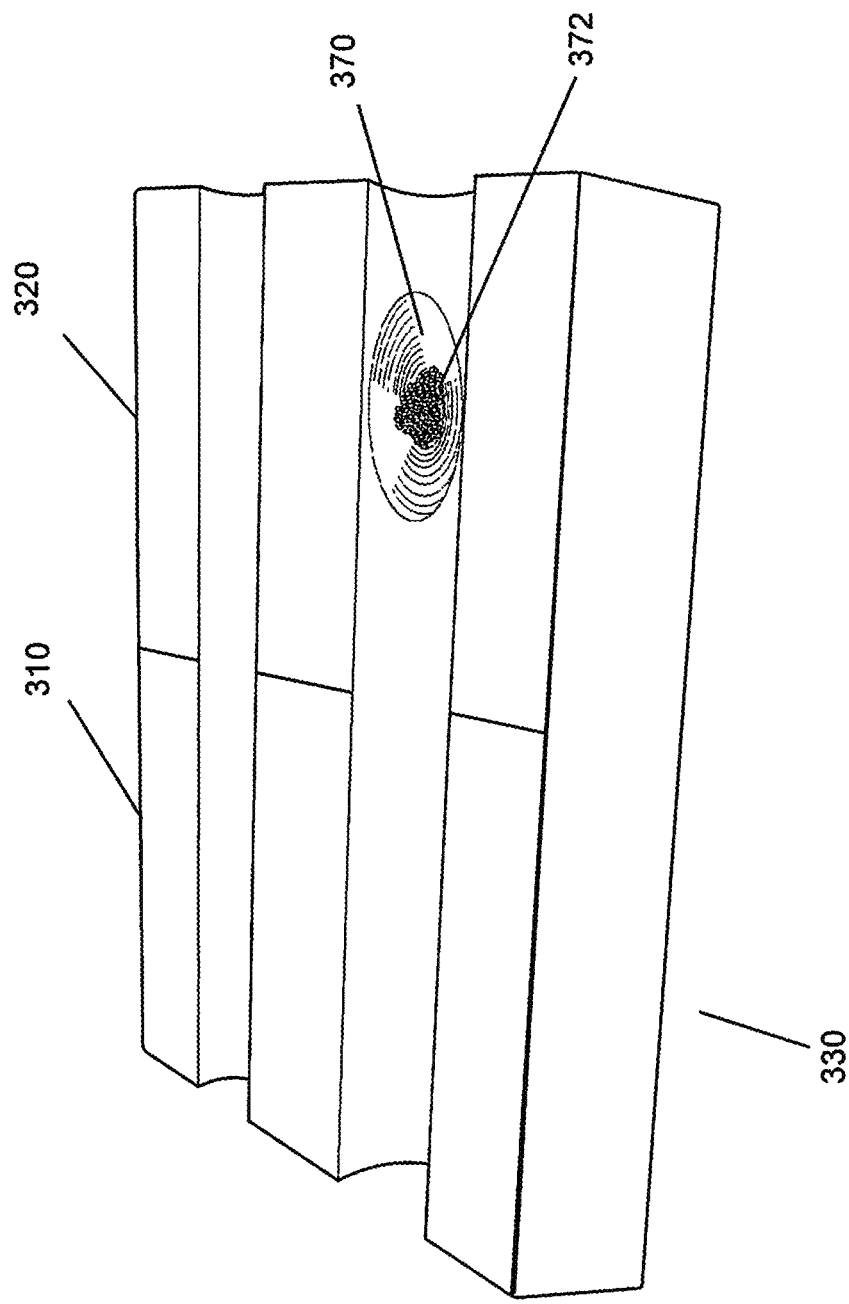
FIG. 9B depicts a perspective view of an assembled implant holding and shaping tray including a mixing surface configured to mix bone material.

FIG. 9B illustrates a perspective view of another embodiment of a tray 330 slidably assembled from a first segment 310 and a second segment 320. In this embodiment, second segment 320 includes a mixing surface 370 in the shape of a bowl, which mixing surface is utilized to mix bone material 372 to hold and to shape a bone implant (not shown).

Figure 9C:
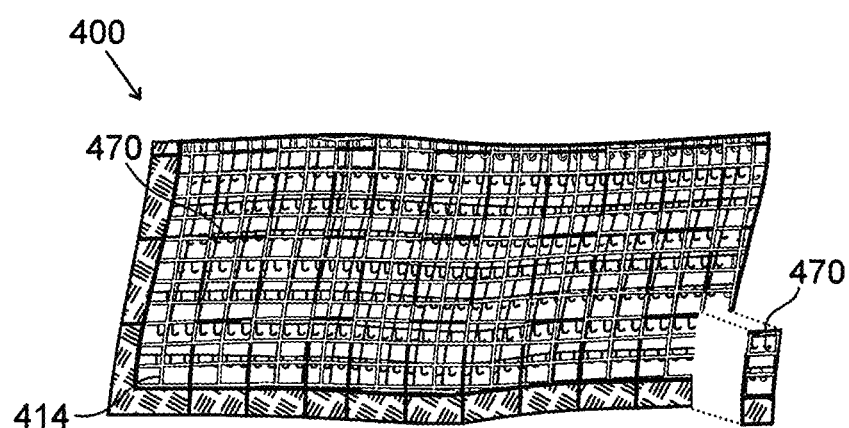
FIG. 9C depicts a perspective view of a bone implant for enclosing bone material. The mesh of the bone implant comprises score lines, colored filaments, or separation assist lines so that a user can easily cut or tear and/or size the mesh prior to or after shaping.

In some embodiments, as shown in FIG. 9C, the bone implant 400 can have score lines or separation assist lines 470 for easy tearing or cutting of the mesh 414. In this manner, the mesh may be used either in its entirety at a surgical site or may be manipulated by a user to separate the mesh into multiple smaller pieces, some or all of which may be used, at a single surgical site or at multiple different surgical sites.

Figure 10A:
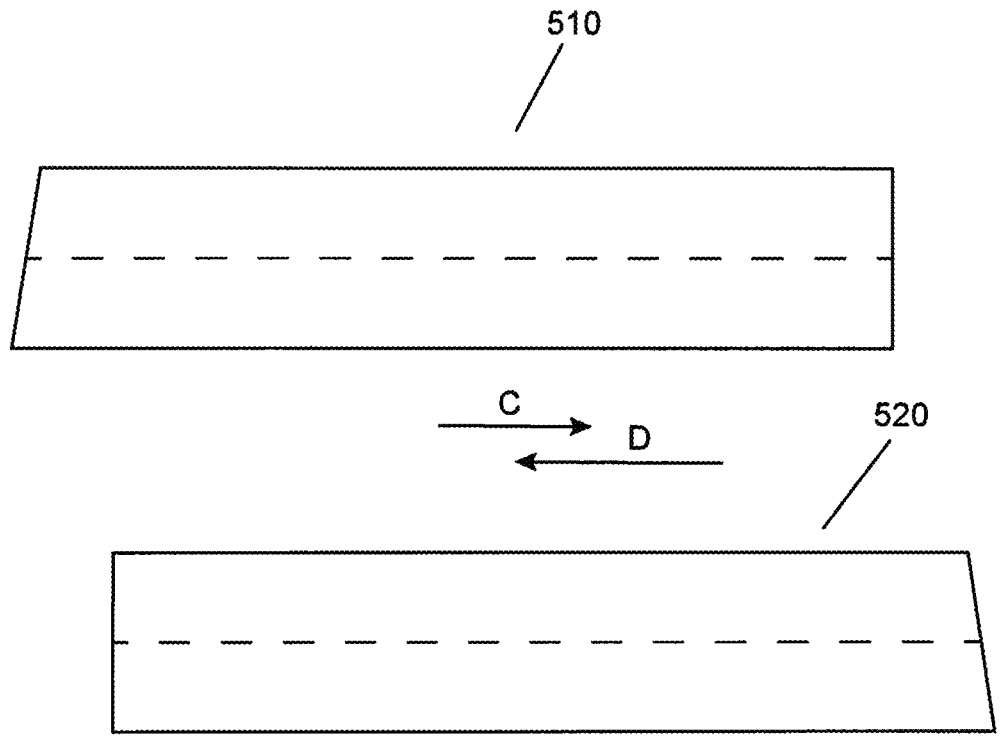
FIG. 10A is a diagram of a first segment and second segment of an unassembled bone implant holding and shaping tray.
Figure 10B:
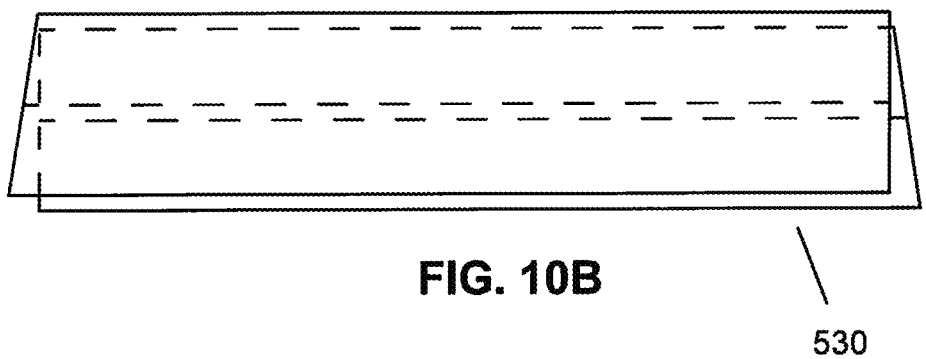
FIG. 10B is a diagram of a stacked or nested assembled bone implant holding and shaping tray.
Figure 11A:
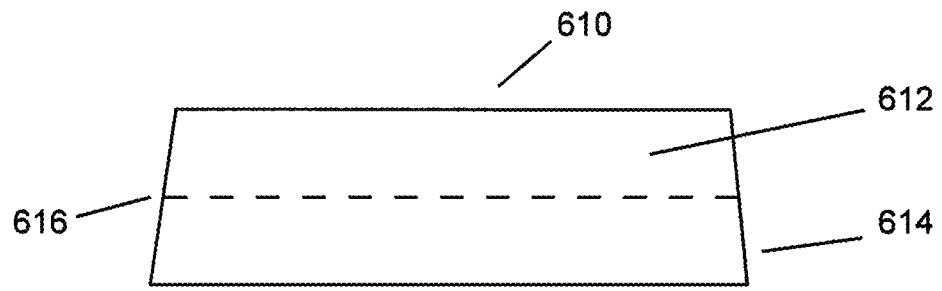
FIG. 11A is a diagram of a first segment of an unassembled bone implant holding and shaping tray.
Figure 11B:
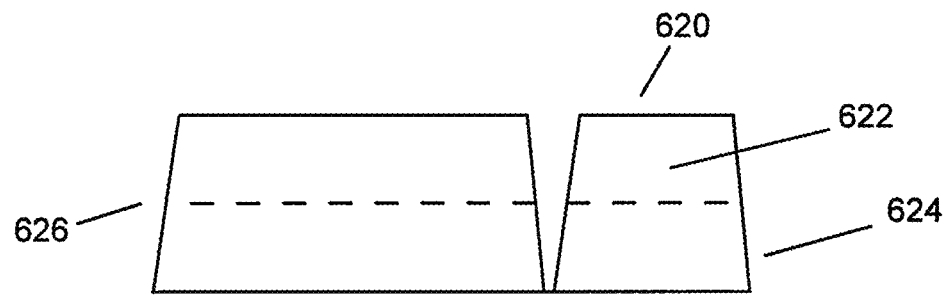
FIG. 11B is a diagram of a second segment of an unassembled bone implant holding and shaping tray, wherein the second segment has a different geometry than that of the first segment.
Figure 11C:
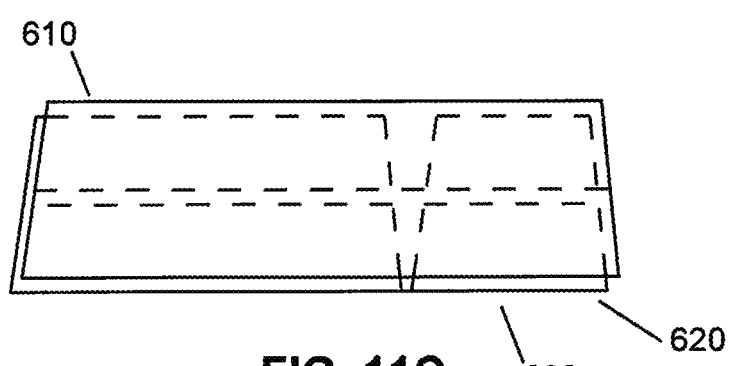
FIG. 11C is a diagram of the first segment stacked or nested on top of the second segment of an assembled bone implant holding and shaping tray.
Figure 11D:
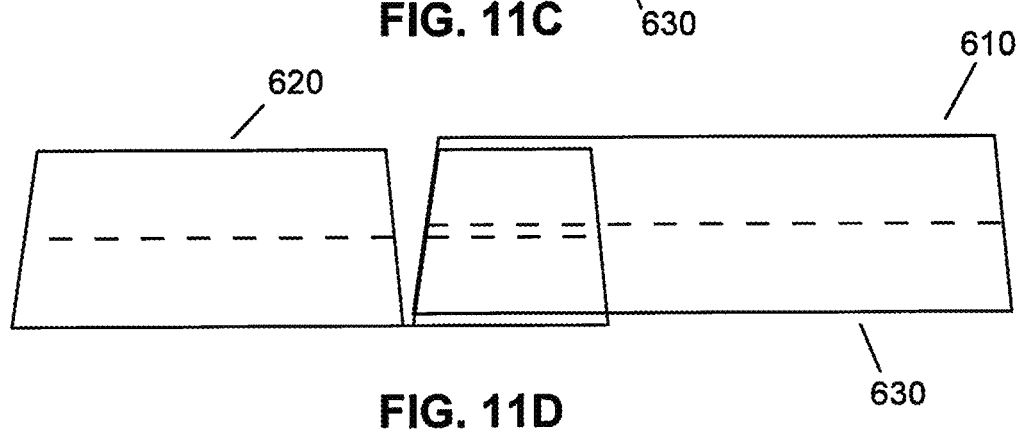
FIG. 11D is a diagram of the assembled bone implant holding and shaping tray in an extended configuration.

FIGS. 10A and 10B are diagrams of another embodiment of the tray of this disclosure. First segment 510 and a second segment 520 can be moved in directions indicated by arrows C and D to be nested on top of each other to form tray 530, which has a small footprint and can be opened into a much longer tray, to hold and to shape a bone implant during surgery, for example. In some embodiments, the first segment and the second segment have infinite variable configurations.

FIGS. 11A, 11B, 11C and 11D are diagrams of yet another embodiment of the tray of this disclosure. In this embodiment, first segment 610 shown in FIG. 11A and second segment 620 shown in FIG. 11B have surfaces with different geometries. First segment 610 has a continuous first surface 612 with solid side walls 614 and 616, while second segment 620 has a discontinuous second surface 622 and solid side walls 624 and 626. Notwithstanding the different geometries of their surfaces, first segment 610 and second segment 620 are illustrated in a nested configuration in FIG. 11C as tray 630 and in an extended configuration in FIG. 11D as extended tray 630.

Figure 12A:
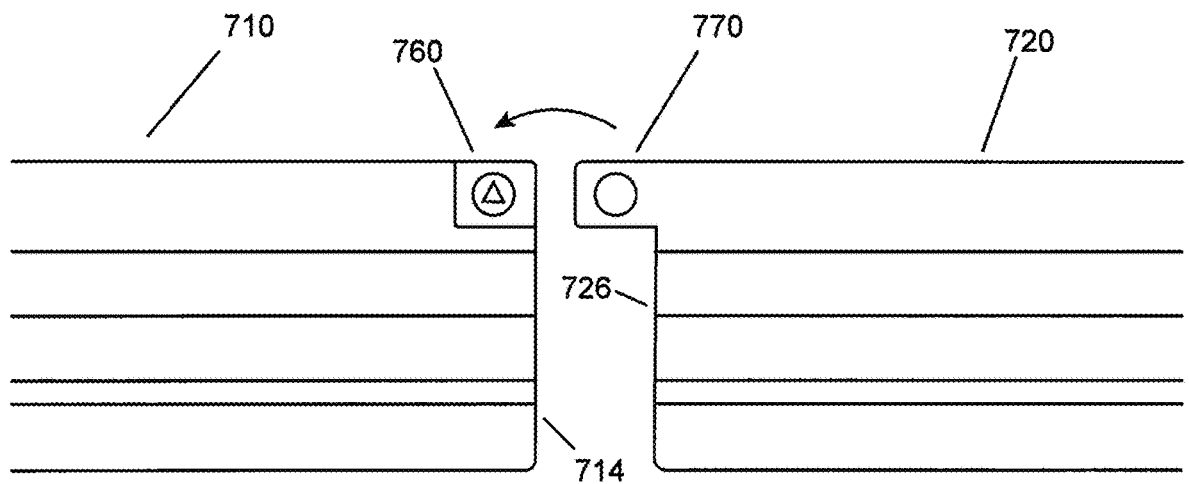
FIG. 12A is a diagram of a first segment and a second segment of an unassembled tray, each segment having a mating part of a mating surface.

In various embodiments, each segment of a tray can be coupled to another segment of the tray and kept in a locked configuration by mating surfaces 52 (FIG. 3). For example, FIG. 12A illustrates a first segment 710 and a second segment 720. First segment 710 has a distal end 714 and second segment 720 has a proximal end 726. First segment 710 and second segment 720 are coupled in a locked configuration by a mating surface that has a first mating part 760 and a second mating part 770. First mating part 760 is disposed at the top of the perimeter of first segment 710 at distal end 714 and configured to receive second mating part 770 disposed at the top of perimeter of second segment 720 at proximal end 726. Second mating part 770 can extend or protrude outwardly to mate with the first mating part 760 of first segment 710 as illustrated in FIG. 12A.

Figure 12B:
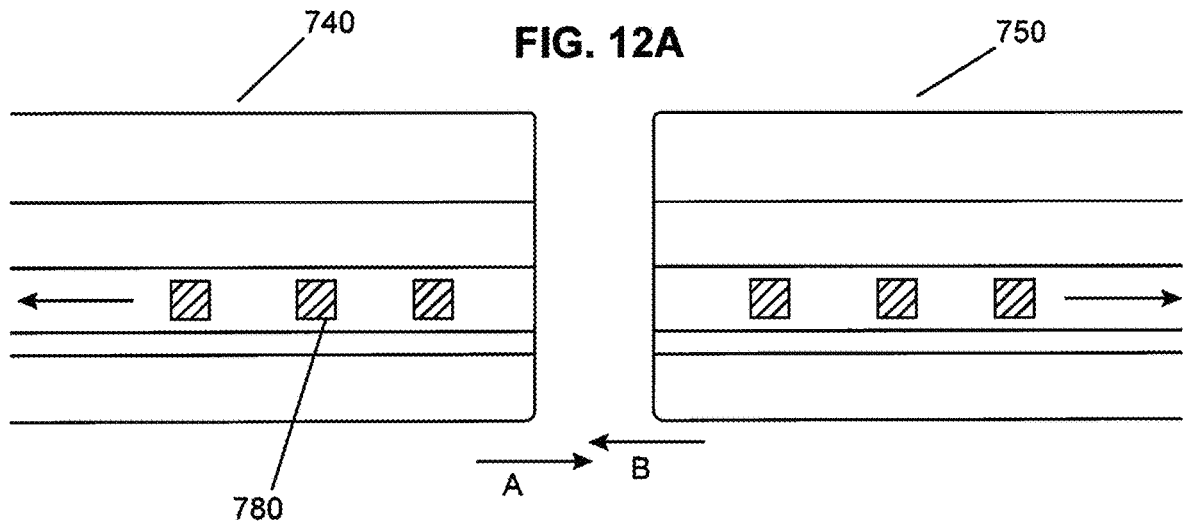
FIG. 12B is a diagram of a first segment and a second segment of an unassembled tray illustrating centrally disposed mating parts of a mating surface.
Figure 12C:
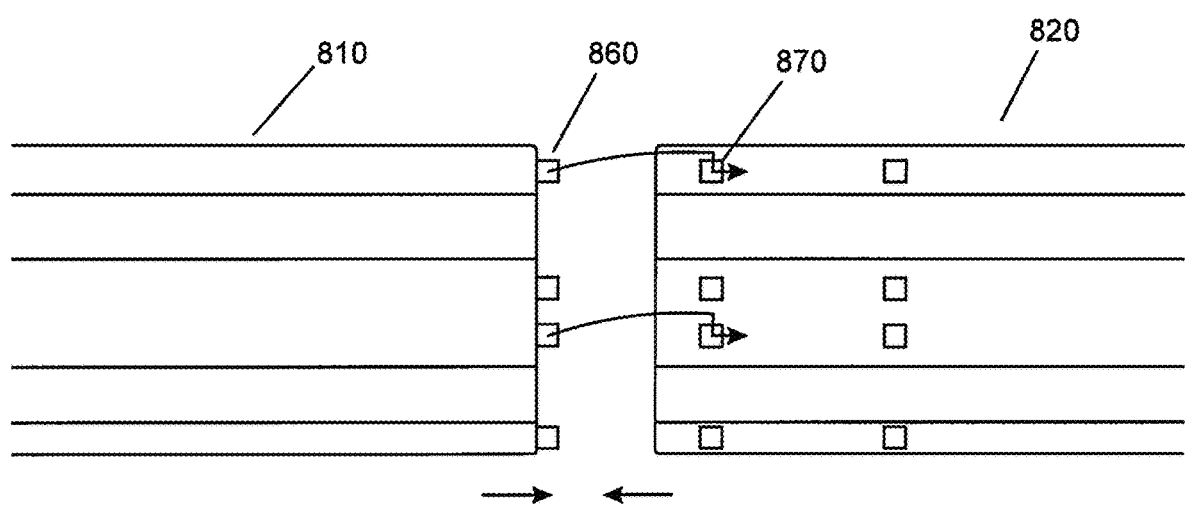
FIG. 12C is a diagram of a first segment and a second segment of an unassembled tray illustrating peripherally and centrally disposed mating parts of a mating surface.
Figure 12D:
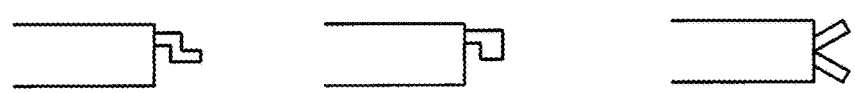
FIG. 12D depicts diagrams of side views of different geometries of hooks that can be used as first and second mating parts of a mating surface.
Figure 12E:
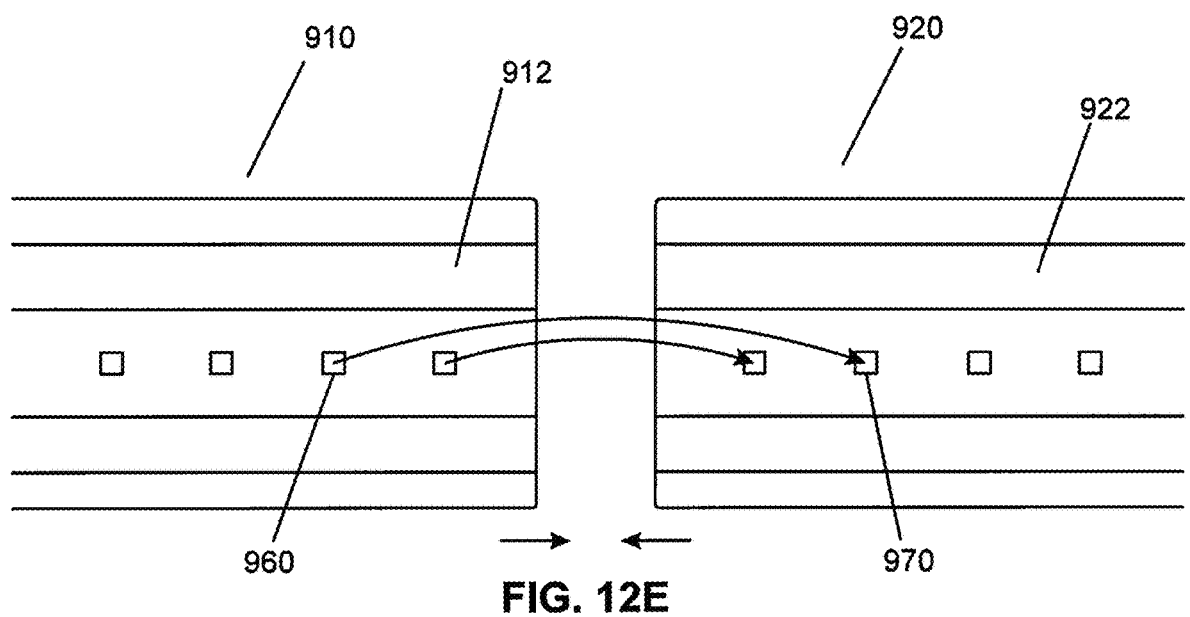
FIG. 12E is a diagram of a first segment and a second segment of an unassembled tray illustrating centrally disposed mating parts of a mating surface.
Figure 12F:
FIG. 12F depicts diagrams of side views of different geometries of hooks that can be used as first and second mating parts of a mating surface.
Figure 13A:
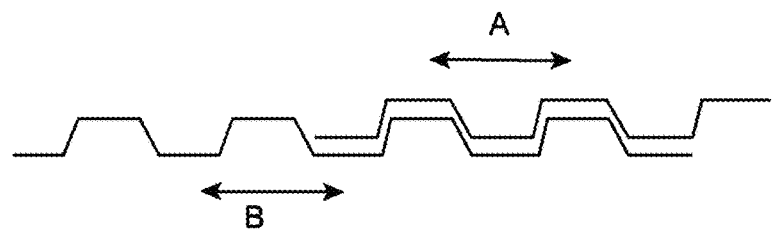
FIG. 13A illustrates a side view of a trapezoidal interference fittings.
Figure 13B:
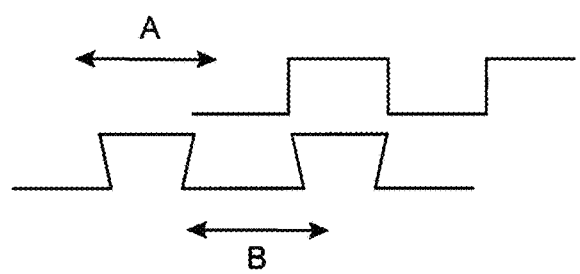
FIG. 13B illustrates a side view of square interference fittings.
Figure 14A:
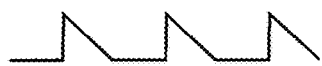
FIG. 14A is a diagram of a toothed interference fitting.
Figure 14B:
FIG. 14B is a diagram of a round semicircular interference fitting.
Figure 14C:
FIG. 14C is a diagram of a square interference fitting.
Figure 14D:
FIG. 14D is a diagram of a trapezoidal interference fitting.
Figure 14E:
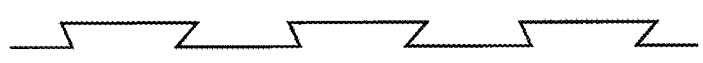
FIG. 14E is a diagram of a dovetail interference fitting.
Figure 14F:
FIG. 14F is a diagram of a spike interference fitting.

Mating surfaces include but are not limited to a variety of fittings, for example, a snap fit fitting, an interference fitting or a tab-slot fitting. Mating surfaces can be located around the perimeter of the first segment or the second segment and/or centrally disposed on the surfaces of these segments as illustrated in FIGS. 12B, 12C and 12E. In FIG. 12B, first segment 740 and second segment 750 have mating parts 780 centrally located on their surfaces. In FIG. 12C, first mating part(s) 860 are located around and protrude from the perimeter of first segment 810 at distal end 814 to mate with the second mating part(s) 870 of mating surfaces provided on second segment 820. In a different embodiment shown in FIG. 12E, first mating part(s) 960 are centrally disposed on the first surface 912 of first segment 910 to lock with second mating part(s) 970 also centrally disposed on the second surface 922 of second segment 920. Side views of different geometries of hooks that can be used as a first and/or second mating parts of mating surfaces useful to lock the first segment and second segment together are illustrated in FIGS. 12D and 12F. Other geometries of interference fittings are illustrated in FIGS. 13A and 13B. FIG. 13A illustrates a side view of trapezoidal interference fittings used in nesting of first segment and second segment wherein arrows A and B indicate movement that would lock the different segments into an assembled tray of extended length. In some embodiments, the first segment and the second segment, while still corresponding to each other, do not possess the same geometric configuration. FIG. 13B illustrates a side view of square interference fittings where a first segment has a square shape and a second segment has a shape having undercuts form less than a 90° angle. Arrows A and B indicate movement that could create a positive lock when the first and second segment are stacked or nested on top of each other. Other side views of geometries for the mating surfaces useful for the trays described in this disclosure are illustrated in FIGS. 14A, 14B, 14C, 14D, 14E, and 14F. In various embodiments, mating surfaces can include, without limitation, geometries such as toothed (FIG. 14A), round semicircular (FIG. 14B), rectangular or square (FIG. 14C), trapezoidal (FIG. 14D), dovetail (FIG. 14E) and spikes (FIG. 14F).

Figure 16:
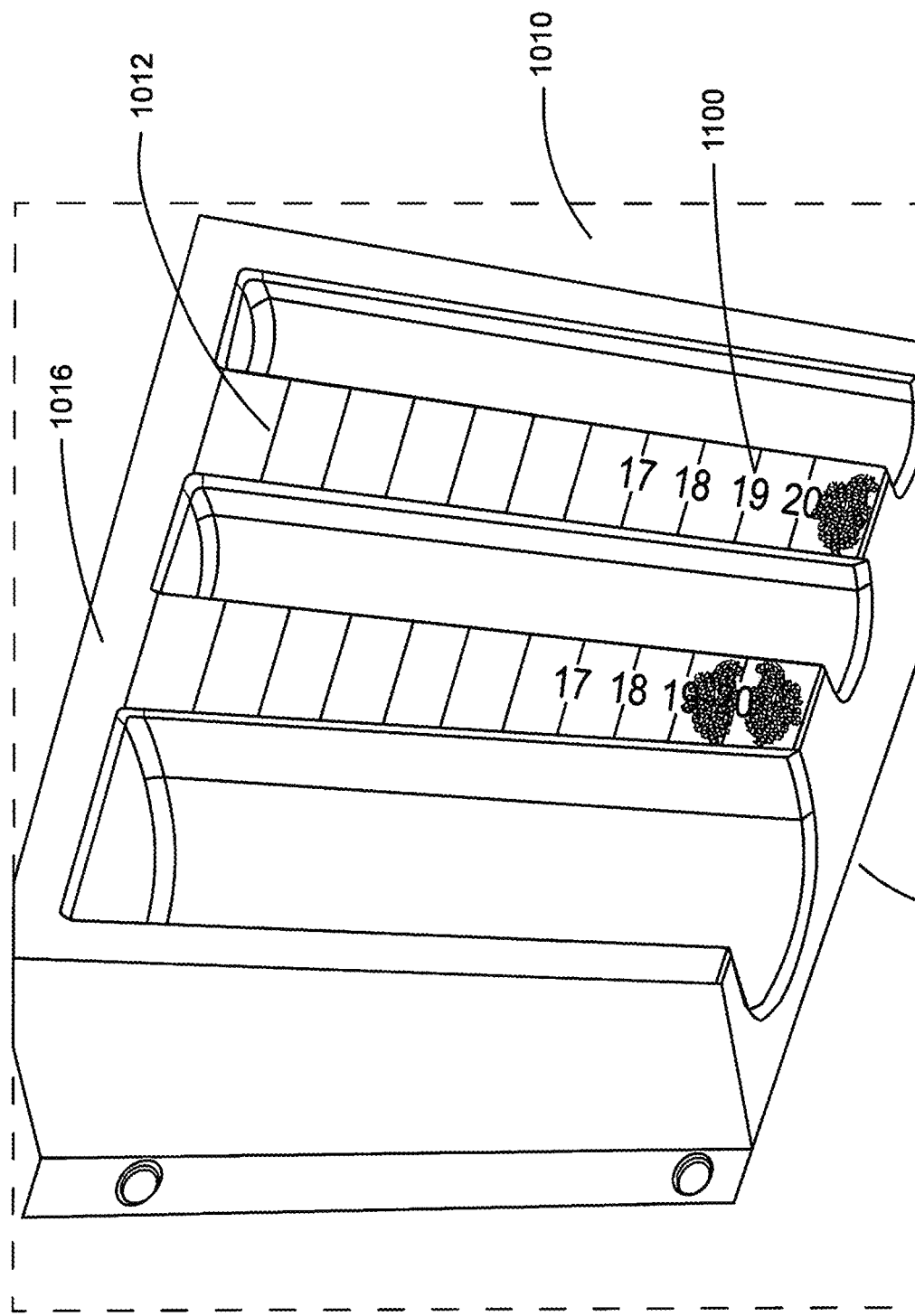
FIG. 16 is a perspective of an unassembled first segment of a bone implant holding and shaping tray having a plurality of markers on its first surface.

In various embodiments, the first surface of the first segment and the second surface of the second segment can have a plurality of markers extending from the distal end of each segment to a region adjacent to the proximal end of each segment, each of the plurality of markers spaced a distance apart from each other such that a measured amount of a bone material can be placed between each marker for a measured dispensing of the bone material into a bone implant and/or to hold and shape the bone implant. FIG. 16 illustrates a first segment 1010 having a first surface 1012 and a plurality of markers 1100 which extend from distal end 1014 to the proximal end 1016 of the first segment 1010. Markers 1100 are spaced a distance apart from each other such that a measured amount of a bone material can be placed between each marker for a measured dispensing of the bone material into a bone implant and/or to hold and shape the bone implant. In some embodiments, the tray can include visual indicia, such as, for example, markings that enable a user to measure defined volumes of material being placed into the bone implant. In some embodiments, the tray can include length and/or volume markings to assist in shaping the bone implant.

In various embodiments, the plurality of segments of the expandable tray of this application can be made from a stamped metal, thermoform, 3D printing, machined materials or an injection molded plastic containing polymers, such as, polyurethane, polyurea, poly ether(amide), PEBA, thermoplastic elastomeric olefin, copolyester, and styrenic thermoplastic elastomer, steel, aluminum, stainless steel, titanium, nitinol, metal alloys with high non-ferrous metal content and a low relative proportion of iron, carbon fiber, glass fiber, plastics, ceramics or a combination thereof. In many aspects, the tray is disposable.

When the tray is made from a thermoform material, the thermoform material may be acrylonitrile butadiene styrene (ABS), polymethyl methacrylate (PMMA, Acrylic, or Plexiglass®), high density polyethylene (HDPE), high impact polystyrene (HIPS), KYDEX™ (PMMA/polyvinyl chloride (PVC) blend), polycarbonate (PC), polyetherimide (PEI or Ultem®), polyethylene terephthalate glycol (PETG), polypropylene (PP), polyvinyl chloride (PVC), thermoplastic polyolefin (TPO).

The tray may also be made from memory shape polymers including, but not limited to, polyethers, polyacrylates, polyamides, polysiloxanes, polyurethanes, polyethers amides, polyurethane/ureas, polyether esters, polynorborene, cross-linked polymers such as cross-linked polyethylene and cross-linked poly(cyclooctene), inorganic-organic hybrid polymers, and copolymers such as urethane/butadiene copolymers, styrene-butadiene copolymers. Memory shape alloys include, but are not limited to TiNi, CuZnAl, and FeNiAl alloys.

Bone Material

In some embodiments, there is an adjustable length bone implant holding and shaping tray that has an initial small footprint and can expand into a larger precision measuring and mixing tray for sizing bone graft and charging bone material into a bone implant. The bone material can be in granular, paste, putty or powder forms.

In some embodiments, the bone material can be demineralized bone material. The demineralized bone material can comprise demineralized bone, powder, chips, granules, shards, fibers or other shapes having irregular or random geometries. These can include, for example, substantially demineralized, partially demineralized, or fully demineralized cortical and cancellous bone. These also include surface demineralization, where the surface of the bone construct is substantially demineralized, partially demineralized, or fully demineralized, yet the body of the bone construct is fully mineralized. The configuration of the bone material can be obtained by milling, shaving, cutting or machining whole bone as described in, for example, U.S. Pat. No. 5,899,939. The entire disclosure is herein incorporated by reference into the present disclosure.

In some embodiments, the bone material can comprise elongated demineralized bone fibers having an average length to average thickness ratio or aspect ratio of the fibers from about 50:1 to about 1000:1. In overall appearance the elongated demineralized bone fibers can be round, spherical, granular, elongated, powders, chips, fibers, cylinders, threads, narrow strips, thin sheets, or a combination thereof. In some embodiments, the bone material comprises elongated demineralized bone fibers and chips. In some embodiments, the bone material comprises fully demineralized fibers and surface demineralized chips. In some embodiments, the ratio of fibers to chips or powders is from about 5, 10, 15, 20, 25, 30, 35, 40, 45, 50, 55, 60, 65 or 70 fibers to about 30, 35, 40, 45, 50, 55, 60, 65, 70, 75, 80, 85, 90 or 95 chips.

In some embodiments, the bone material comprises demineralized bone matrix fibers and demineralized bone matrix chips in a 30:60 ratio. In some embodiments, the bone material comprises demineralized bone matrix fibers and demineralized bone matrix chips in a ratio of 25:75 to about 75:25 fibers to chips.

In some embodiments, the bone material can be an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the bone material can comprise mineral particles, which comprise tricalcium phosphate and hydroxyapatite in a ratio of about 80:20 to about 90:10. In some embodiments, the mineral particles can comprise tricalcium phosphate and hydroxyapatite in a ratio of about 70:30 to about 95:5. In some embodiments, the mineral particles can comprise tricalcium phosphate and hydroxyapatite in a ratio of about 85:15.

In some embodiments, the bone material may be seeded with harvested bone cells and/or bone tissue, such as for example, cortical bone, autogenous bone, allogenic bones and/or xenogeneic bone while it is mixed.

In some embodiments, the bone material may be mixed with one or more therapeutic agents, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof. Recombinant BMP-2 can be used at a concentration of about 0.4 mg/mL to about 10.0 mg/mL, preferably about 1.5 mg/mL.

The bone material may include or be mixed with one or more members from the TGF-β superfamily. For example, the matrix may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The bone material may include or be mixed with a therapeutic agent including, but not limited to, IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. The bone material may include or be mixed with therapeutic agents including excitatory amino acids such as glutamate and aspartate, antagonists or inhibitors of glutamate binding to NMDA receptors, AMPA receptors, and/or kainate receptors. The bone material may include or be mixed with therapeutic agents to reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

The bone material may include or be mixed with a therapeutic agent including, but not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The bone material may include or be mixed with a therapeutic agent including, but not limited to, an anti-inflammatory agent. An example of an anti-inflammatory agent includes, but is not limited to, clonidine, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The bone material may include or be mixed with a therapeutic agent including, but not limited to, a statin. Examples of a useful statin include, but are not limited to, atorvastatin, simvastatin, pravastatin, cerivastatin, mevastatin (see U.S. Pat. No. 3,883,140, the entire disclosure of which is herein incorporated by reference), velostatin (also called synvinolin; see U.S. Pat. Nos. 4,448,784 and 4,450,171; these entire disclosures are herein incorporated by reference), fluvastatin, lovastatin, rosuvastatin and fluindostatin (Sandoz XU-62-320), dalvastain (European Publication No. EP738510A2, the entire disclosure of which is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the bone material can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium;

cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

The antimicrobial agent in the bone material can be an antiviral agent that can be mixed with the bone material. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

In various embodiments, one or more components of the bone material utilized in the trays described in this disclosure are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply into the bone material dispensing apparatus. Gamma rays are highly effective in killing microorganisms, they leave no residues, nor do they have sufficient energy to impart radioactivity to the apparatus. Gamma rays can be employed when the apparatus is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the bone material dispensing apparatus. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly charged streams of electrons generated by the acceleration and conversion of electricity.

Other methods may also be used to sterilize the dispensing apparatus including, but not limited to, gas sterilization such as, for example, with ethylene oxide or steam sterilization.

Mesh

The mesh of the instant application may be made from woven threads that are configured to allow ingrowth of cells while also retaining the bone material within the compartment of the bone implant. The threads of the mesh may have a predetermined thickness of about 0.01 mm to about 2.0 mm, about 0.05 mm to about 1.0 mm, or about 0.1 to about 0.5 mm. The thickness of the threads may be uniform along the length of each thread or varied across the length of each thread. In some embodiments, some threads have a greater thickness than other threads. The threads may be sized to allow for customizable pore sizes between the threads. In some embodiments, the bone implant is configured to facilitate transfer of substances and/or materials surrounding the surgical site. Upon implantation to a surgical site, the bone implant may participate in, control, or otherwise adjust, or may allow penetration of the mesh by surrounding materials, such as cells or tissue.

The mesh may be sized according to the needs of a particular application. For example, the mesh may include dimensions between about 1 mm to about 100 mm in diameter. In some embodiments, the mesh includes a diameter of about 5 mm, 10 mm, 15 mm, 20 mm, 25 mm, 30 mm, 35 mm, 40 mm, 45 mm, 50 mm, 55 mm, 60 mm, 65 mm, 70 mm, 75 mm, 80 mm, 85 mm, 90 mm, 95 mm, or 100 mm. In some embodiments, the mesh includes a length or depth between about 0.1 cm to about 10 cm. In some embodiments, the mesh includes a length or depth of about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, 25 cm, 26 cm, 27 cm, 28 cm, 29 cm, 30 cm, 31 cm, 32 cm, 33 cm, 33 cm, 34 cm, 35 cm, 36 cm, 37 cm, 38 cm, 39 cm, 40 cm, 41 cm, 42 cm, 43 cm, 44 cm, 45 cm, 46 cm, 47 cm, 48 cm, 49 cm, or 50 cm.

In some embodiments, the mesh can have selected dimensions, such as, for example, a diameter of 0.5 cm and a length of 0.1 cm, providing a volume of 0.02 cc. In other embodiments, the mesh can have a diameter of 1 cm and a length of 1 cm, providing a volume of 0.79 cc. In yet other embodiments, a mesh bag has a diameter of 1.5 cm and length of 3 cm, providing a volume of 5.3 cc.

The shape, mesh size, thickness, and other structural characteristics, of the mesh, for example, architecture, may be customized for the desired application. For example, to optimize cell or fluid migration through the mesh, the pore size may be optimized for the viscosity and surface tension of the fluid or the size of the cells. For example, pore sizes between threads on the order of approximately 100-200 µm may be used if cells are to migrate through the mesh. In other embodiments, wave-shaped threads may be extruded to have larger peaks and crests and the size of the pores may be larger. For example, in some embodiments, the pore size between threads may be about 0.1 mm to about 5 mm, about 0.5 mm to about 3 mm, or about 1 mm to about 2 mm. Mesh size may be controlled by physically weaving strands and by controlling the thickness of threads.

The mesh may have varying degrees of permeability across its surface. It may be permeable, semi-permeable, or non-permeable. Permeability may be with respect to cells, to liquids, to proteins, to growth factors, to bone morphogenetic proteins, or other. In further embodiments, the material may be braided.

The mesh may have any suitable custom configuration. For example, the mesh can have a variety of shapes, such as, for example, a ring, a cylinder, a cage, a rectangular shape, a suture-like wrap, a continuous tube, or other configurations. The mesh may be formed as a thin tube designed to be inserted through catheters or an introducer tube; a rectangular shape designed to fit adjacent to spinal processes for posterolateral spine fusion; a cube; a rectangular prism like structure designed to fit between vertebral bodies or within cages for interbody spinal fusion; a tube-like shape; relatively flat shapes; rectangular shapes; structures pre-shaped to fit around various implants (e.g., dental, doughnut with hole for dental implants); or relatively elastic ring-like structures that will stretch and then conform to shapes (e.g., rubber band fitted around processes).

Additionally, in some embodiments, the flexible character of the mesh allows for the mesh to be manipulated into a plurality of compartments. For example, in a tubular embodiment, the tube may be formed into a plurality of compartments by tying a cord around the tube at one or more points, or by other suitable mechanism such as crimping, twisting, knotting, stapling, or sewing.

In certain embodiments, a bone void can be shaped by the mesh containing bone material. A compartment within mesh can be at least partially shaped with a bone repair substance. In various embodiments, at least partially shaped as used herein, can mean that a percentage of the volume of a compartment or hollow interior region is at least 70% occupied, at least 75% occupied, at least 80% occupied, at least 85% occupied, at least 90% occupied, at least 95% occupied, or 100% occupied. The mesh can be inserted into an opening in the defect until the defect is substantially shaped. In various embodiments, substantially shaped, as used herein, can mean that a percentage of the volume of a defect is at least 70% occupied, at least 75% occupied, at least 80% occupied, at least 85% occupied, at least 90% occupied, at least 95% occupied, or 100% occupied.

In some embodiments, the mesh may be labeled. Such labeling may be done in any suitable manner and at any suitable location on the mesh. In some embodiments, labeling may be done by using a silk screen printing, using an altered weaving or knotting pattern, by using different colored threads, or other means. The labeling may indicate information regarding the mesh. Such information might include a part number, donor ID number, number, lettering or wording indicating order of use in the procedure or implant size, etc. In some embodiments, the mesh can be a specific color to help provide the correct orientation of the mesh prior to or during shaping and to confirm that the plurality of projections and/or plurality of recesses of the mesh are oriented to optimize their engagement. In some embodiments, a portion of the mesh or the entire mesh is colored blue, purple, pink, orange, yellow, green, or red.

In certain embodiments, the mesh can be made of yarn that is monofilament or multifilament, and the yarn can be knitted, woven, non-woven shape memory, felted, pointbonded, additive manufactured, such as 3-D printed or a combination thereof. A weave pattern can be selected to impart flexibility and stretchable characteristics to the mesh.

The mesh can have a weave density of from about 8 to about 400 filaments, such as fibers per inch. The mesh can have a weave density from about 8 to about 375 filaments fibers per inch, from about 8 to about 350 fibers per inch, from about 8 to about 300 fibers per inch, from about 8 to about 250 fibers per inch, from about 8 to about 200 fibers per inch, from about 20 to about 350 fibers per inch, from about 20 to about 300 fibers per inch, from about 20 to about 250 fibers per inch, from about 20 to about 200 fibers per inch, from about 50 to about 350 fibers per inch, from about 50 to about 300 fibers per inch, from about 50 to about 250 fibers per inch, from about 50 to about 200 fibers per inch, from about 100 to about 350 fibers per inch, from about 100 to about 300 fibers per inch, from about 100 to about 250 fibers per inch, or from about 100 to about 200 fibers per inch. The mesh can have a weave density from about 8, 10, 15, 20, 25, 30, 35, 40, 45, 50, 55, 60, 65, 70, 75, 80, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345 to about 350 fibers per inch.

The material and configuration of the mesh may be selected or adjusted based on desired release characteristics. Specific properties of the mesh that may be adjusted include thickness, permeability, porosity, strength, flexibility, and/or elasticity. In some embodiments, the thickness and porosity of the mesh may contribute to its strength, flexibility, and elasticity. In some embodiments, the mesh may be made of a squishy, moldable, sticky, and/or tacky material to facilitate placement and packing of the bone implant to a surgical site.

The average molecular weight of the polymer used to make the mesh can be from about 1,000 to about 10,000,000; or about 1,000 to about 1,000,000; or about 5,000 to about 500,000; or about 10,000 to about 100,000; or about 20,000 to 50,000 g/mol. In some embodiments, the molecular weight of the polymer is 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 125,000, 150,000, 175,000, 200,000, 225,000, 250,000, 275,000, 300,000, 325,000, 350,000, 375,000, 400,000, 425,000, 450,000, 475,000, 500,000, 525,000, 550,000, 575,000, 600,000, 625,000, 650,000, 675,000, 700,000, 725,000, 750,000, 775,000, 800,000, 825,000, 850,000, 875,000, 900,000, 925,000, 950,000, 975,000 and/or 1,000,000 Daltons.

The mesh may have varying degrees of permeability. It may be permeable, semi-permeable, or non-permeable. Permeability may be with respect to cells, to liquids, to proteins, to growth factors, to bone morphogenetic proteins, or other substances. The mesh may be 1 to about 30% permeable, from about 30 to about 70% permeable, or from about 70 to about 95% permeable. The mesh may be 1, 5, 10, 15, 20, 25, 30, 35, 40, 45, 50, 55, 60, 65, 70, 75, 80, 85, 90, 95, 96, 97, 98, or 99% permeable. In alternative embodiments, the mesh may comprise a substantially solid structure, such as a polymer structure with a chamber, or a spun cocoon.

The mesh can be a porous mesh such that fluid transfer and cell infiltration can occur so that osteoblasts can manufacture bone graft. The porous mesh can have a pore size of from about 1 micron to about 2000 microns, from about 1 micron to about 1500 microns, from about 1 micron to about 1000 microns, from about 1 micron to about 500 microns, from about 1 micron to about 250 microns, from about 100 micron to about 2000 microns, from about 150 to about 1500 microns, from about 200 to about 1000 microns, from about 250 to about 500 microns. In some embodiments, the pore size can be about 1, 10, 20, 50, 80, 100, 120, 150, 180, 200, 220, 250, 280, 300, 350, 400, 450, 500, 550, 600, 650, 700, 750, 800, 850, 900, 950, 1000, 1250, 1450, 1650, 1850, and/or 2000 microns.

In some embodiments, the mesh can fully enclose the bone material, where the mesh surrounds the entire bone material (e.g., bone particles, bone cement, etc.) to fully enclose it. In some embodiments, the mesh can partially enclose the bone material (e.g., bone particles, bone cement, etc.), where the mesh surrounds a portion of the bone material leaving a portion of the bone material that is not enclosed by the mesh.

The bone material of the bone implant can comprise fully demineralized bone fibers and surface demineralized bone chips. The bone material may also comprise fibers, powder, chips, triangular prisms, spheres, cubes, cylinders, shards or other shapes having irregular or random geometries. These can include, for example, "substantially demineralized," "partially demineralized," or "fully demineralized" cortical and/or cancellous bone. These also include surface demineralization, where the surface of the bone construct is substantially demineralized, partially demineralized, or fully demineralized, yet the body of the bone construct is fully mineralized.

In some embodiments, the bone implant is configured to self-seal and to seal and enclose the bone material via chemical fusion, heat treatment, self-fusing materials, self-adhering materials, adhesives, solvent treatment, suturing, knotting or a combination thereof. In some embodiments, adhesives that can be used include, but are not limited to cyanoacrylates (such as histoacryl, B Braun, which is n-butyl-2 cyanoacrylate; or Dermabond, which is 2-octyl-cyanoacrylate), epoxy-based compounds, dental resin sealants, dental resin cements, glass ionomer cements, polymethyl methacrylate, gelatin-resorcinol-formaldehyde glues, collagen-based glues, inorganic bonding agents such as zinc phosphate, magnesium phosphate or other phosphate-based cements, zinc carboxylate, L-DOPA (3,4-dihydroxy-L-phenylalanine), proteins, carbohydrates, glycoproteins, mucopolysaccharides, other polysaccharides, hydrogels, protein-based binders such as fibrin glues and mussel-derived adhesive proteins, and any other suitable substance. In some embodiments, the bone implant is sealable (permanently or temporarily) via mechanical means such as, for example, zippers, sutures, staples, pins, snaps, clips, hooks, loops, or a combination thereof.

In some embodiments, the bone implant includes a plurality of projections that can be hooks and the plurality of recesses that can be loops, similar to Velcro® that can be used to enclose the bone material into the implant. Alternatively, the hook and loop mating is absorbable Velcro®.

In some embodiments, the mesh can be pre-cut, perforated and/or notched so that a user can easily cut, tear and/or size the mesh prior to or after shaping. In some embodiments, as shown in FIG. 9C, the bone implant 400 can have score lines or separation assist lines 470 for easy tearing of the mesh 414. In this manner, the mesh may be used either in its entirety at a surgical site or may be manipulated by a user to separate the mesh into multiple smaller pieces, some or all of which may be used, at a single surgical site or at multiple different surgical sites. The score lines or separation assist lines afford the user an ability to conveniently adjust the size of the mesh based upon the size of the defect to be shaped or other factors noted in the operational field, which can help to assure that a mesh volume of an appropriate size is used. For example, this can help to assure that the use of an inappropriately oversized mesh is avoided, e.g. one which would be packed into a defect under too much compression thus potentially leading to an undesired increase in the spatial density or concentration of an osteoconductive and/or osteoinductive bone material in the mesh, and/or creating too much compression on surrounding soft or hard tissues, or that the use of an inappropriately undersized mesh is avoided, e.g. one that would be packed into a defect too loosely. In some embodiments, the mesh can be shaped with bone material, sealed closed, and then torn at the score lines or separation assist lines. Alternatively, the mesh can be torn first at the score lines or separation assist lines, shaped with bone material, and then sealed.

In some embodiments, a portion of the mesh or the entire mesh can be pre-folded and/or contain bent sections that enable a user to create pre-selected shapes and/or patterns from the mesh. In some embodiments, the mesh can be pre-folded and/or contain bent sections that are configured into a box or tube shape.

The mesh may comprise a penetrable material at a first compartment configured for placement adjacent bone and a substantially impenetrable material at a second compartment configured for placement adjacent soft tissue. For example, the pore size between the threads at a first region of the mesh may be sized large enough to allow cell migration through the mesh, but the pore size between the threads at a second region of the may be sized small enough (or may include a lack of pores altogether) to prevent cell migration. Alternatively, the material of the mesh may have a uniform configuration such that adjacent compartments may have substantially identical characteristics. By way of example only, the mesh may have a porous surface that is positioned adjacent bone, and a separate or opposite surface that has a generally impenetrable surface that is positioned adjacent soft tissue. Alternatively, the mesh may have one compartment that comprises a porous material, and a second compartment that comprises a substantially impenetrable material.

For either single or multi-compartment bone implants, the mesh may be closed after shaping substances. Accordingly, the bone implant may be provided in an unshaped, unsealed state. After a substance for delivery is placed in the bone implant, the mesh of the bone implant may be permanently or temporarily closed by the plurality of projections and/or the plurality of recesses. Further, temporary closure may be by tying, fold lock, cinching, or other means. A temporarily closed bone implant can be opened without damaging the mesh during surgical implantation to add or remove substances in the bone implant. In some embodiments, the mesh is foldable in a closed configuration so as to enclose the bone material within the inner surface of the mesh. The mesh can be manually or mechanically folded either during manufacture or prior to a surgical procedure.

In some embodiments, biological attachment may be via mechanisms that promote tissue ingrowth such as by a porous coating or a hydroxyapatite-tricalcium phosphate (HA/TCP) coating. Generally, hydroxyapatite bonds by biological effects of new tissue formation. Porous ingrowth surfaces, such as titanium alloy materials in a beaded coating or tantalum porous metal or trabecular metal may be used and facilitate attachment at least by encouraging bone to grow through the porous implant surface. These mechanisms may be referred to as biological attachment mechanisms. In some embodiments, the bone implant may be attached to a tissue structure through a wrap, a suture, a wire, a string, an elastic band, a cable or a cable tie, or a combination thereof or another fastener.

In other embodiments, suitable materials that form the mesh of the bone implant include natural materials, synthetic polymeric resorbable materials, synthetic polymeric non-resorbable materials, and other materials. Natural mesh materials include silk, extracellular matrix (such as DBM, collagen, ligament, tendon tissue, or other), silk-elastin, elastin, collagen, and cellulose. Synthetic polymeric resorbable materials include poly(lactic acid) (PLA), poly(glycolic acid) (PGA), poly(lactic acid-glycolic acid) (PLGA), polydioxanone, PVA, polyurethanes, polycarbonates, and others.

In various embodiments, the mesh comprises a polymer matrix. In some embodiments, DBM fibers and/or DBM powder are suspended in the polymer matrix to facilitate transfer of cells into and out of the mesh bag to induce bone growth at the surgical site. In other embodiments, the mesh further comprises mineralized bone fibers suspended in a polymer matrix. In some embodiments, the DBM powder is suspended in the polymer matrix between the DBM fibers and the mineralized bone fibers. In some embodiments, the DBM powder is suspended between the DBM fibers in the polymer matrix so as to reduce and/or eliminate gaps that exist between the fibers. In some embodiments, the DBM powder is suspended between the DBM fibers in the polymer matrix to improve osteoinductivity for facilitating bone fusion, for example, interspinous process fusion.

In some embodiments, the polymer matrix comprises a bioerodible, a bioabsorbable, and/or a biodegradable biopolymer that may provide immediate release or sustained release. Examples of suitable sustained release biopolymers include, but are not limited to, poly (alpha-hydroxy acids), poly (lactide-co-glycolide) (PLGA), polylactide (PLA), polyglycolide (PG), polyethylene glycol (PEG), conjugates of poly (alpha-hydroxy acids), poly(orthoester)s (POE), polyaspirins, polyphosphagenes, collagen, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), or combinations thereof. mPEG and/or PEG may be used as a plasticizer for PLGA, but other polymers/excipients may be used to achieve the same effect. mPEG imparts malleability to the polymer. In some embodiments, these biopolymers may also be coated on the mesh to provide a desired release profile or ingrowth of tissue. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the substance from the bone implant. In some embodiments, the range of the coating on the mesh ranges from about 5 microns to about 250 microns or 5 microns to about 200 microns.

In some embodiments, various components of the mesh comprises poly(lactide-co-glycolide) (PLGA), polylactide (PLA), polyglycolide (PGA), D-lactide, D,L-lactide, L-lactide, D,L-lactide-co-ε-caprolactone, D,L-lactide-co-glycolide-co-ε-caprolactone, L-lactide-co-ε-caprolactone or a combination thereof.

In some embodiments, the mesh further comprises bone morphogenic proteins (BMPs), growth factors, antibiotics, angiogenesis promoting materials, bioactive agents or other actively releasing materials.

The mesh may be used to deliver a substance comprising any suitable biocompatible material. In specific embodiments, the mesh may be used to deliver surface demineralized bone chips, optionally of a predetermined particle size, fully demineralized bone fibers, optionally pressed, and/or allograft. For embodiments where the substance is a biologic, the substance may be autogenic, allogenic, xenogenic, or transgenic. Other suitable materials that may be positioned in the mesh include, for example, protein, nucleic acid, carbohydrate, lipids, bone stimulating substances, particulate metal, metal salts, vitamins, nutraceuticals, sugars, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, DBM, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above.

In accordance with some embodiments, the material to be positioned in the hollow compartment of the mesh may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic sub stances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases and the like; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other member; tissue transplants; autogenous tissues such as blood, serum, soft tissue, bone marrow, or the like; bioadhesives; bone morphogenetic proteins (BMPs including BMP-2); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

The material may have functional characteristics. Alternatively, other materials having functional characteristics may be incorporated into the mesh. Functional characteristics may include radiopacity, bacteriocidity, source for released materials, tackiness, etc. Such characteristics may be imparted substantially throughout the mesh or at only certain positions or portions of the mesh.

Suitable radiopaque materials include, for example, ceramics, mineralized bone, ceramics/calcium phosphates/calcium sulfates, metal particles, fibers, and iodinated polymer (see, for example, WO/2007/143698). Polymeric materials may be used to form the mesh and be made radiopaque by iodinating them, such as taught for example in U.S. Pat. No. 6,585,755, herein incorporated by reference in its entirety. Other techniques for incorporating a biocompatible metal or metal salt into a polymer to increase radiopacity of the polymer may also be used. Suitable bacteriocidal materials may include, for example, trace metallic elements. In some embodiments, trace metallic elements may also encourage bone growth.

In some embodiments, the mesh may comprise a material that becomes tacky upon wetting. Such material may be, for example, a protein or gelatin-based material. Tissue adhesives, including mussel adhesive proteins and cryanocrylates, may be used to impart tackiness to the mesh. In further examples, alginate or chitosan material may be used to impart tackiness to the mesh. In further embodiments, an adhesive substance or material may be placed on a portion of the mesh or in a particular region of the mesh to anchor that portion or region of the mesh in place at a surgical site.

Methods of Use

A method of shaping bone material into a bone implant is provided. The method comprises providing a tray having a first segment having a distal end, and a first surface sized to hold and shape at least a portion of the bone implant with bone material. The tray includes a second segment having a second surface sized to hold and shape at least a portion of the bone implant with bone material, the second segment having a proximal end configured to be coupled to the distal end of the first segment so as to extend the first surface to hold and shape the bone implant as illustrated in FIGS. 1 and 2. A bone implant is provided which comprises a mesh having an inner surface and an outer surface opposing the inner surface, the inner surface configured to receive the bone material when the inner surface is in the open configuration; disposing the bone material into the inner surface of the mesh by orienting the mesh in the open configuration; and enclosing the bone material in the mesh by orienting the mesh in the closed configuration. In some embodiments, the bone implant is sealable via mechanical means such as, for example, zippers, sutures, staples, pins, snaps, clips or a combination thereof. In other embodiments, the bone implant includes a plurality of projections that can be hooks and a plurality of recesses that can be loops similar to Velcro® that can be used to enclose the bone material into the implant. Alternatively, the hook and loop mating is absorbable Velcro®.

In another embodiment another method of shaping bone material into a foldable container is provided. The method comprises providing a first segment having a bottom surface, and a first surface sized to hold and shape at least a portion of the bone implant with bone material; and the tray comprising a second segment having a second surface sized to hold and shape at least a portion of the bone implant with bone material, the second segment having a top surface configured to be coupled to the bottom surface of the first segment, so as to extend the first surface to hold and shape the bone implant; providing the bone implant comprising a mesh having an inner surface and an outer surface opposing the inner surface, the inner surface configured to receive the bone material when the inner surface is in the open configuration; and disposing the bone material into the inner surface of the mesh by orienting the mesh in the open configuration; and enclosing the bone material in the mesh by orienting the mesh in the closed configuration.

The bone material can be mixed with liquid material and, optionally, a therapeutic agent using a spatula on the mixing surface of the tray, as illustrated in FIG. 9B, until the desired consistency of the bone material is achieved (e.g., putty, paste, etc.). The bone material can be mixed with a suitable diluent and then loaded into the bone implant, for example a bag. In some embodiments, the diluent includes dextrose, other sugars including but not limited to sucrose, fructose, glucose, lactated ringer's, polyols including but not limited to mannitol, xylitol, sorbitol, maltitol, lactitol, polysaccharides including but not limited to native or pre-gelatinized starch, maltodextrins, cyclodextrins, mineral compounds including but not limited to dicalcium or tricalcium phosphate, either dihydrate or anhydrous, cellulose derivatives including but not limited to microcrystalline cellulose, lactoses either monohydrates thereof or anhydrous, as well as their mixtures such as dicalcium phosphate dihydrate, mannitol, pre-gelatinized maize starch, microcrystalline cellulose and their mixtures, water and/or NaCl (saline). In some embodiments, the saline is 0.90% saline or 0.45% saline. In some embodiments, other delivery vehicles can be used for example, D5W (dextrose in 5% water), D5NS (dextrose in 5% water and normal saline) and D5W/1/2NS (D5W and ½ normal saline), blood, mesenchymal stem cells, or the like.

The bone implant holding and shaping tray can be used to treat a variety of conditions including osteoporosis, bone fracture repair or healing, dental procedures for which increased bone formation in the jaw is of clinical benefit, repair of craniofacial bone defects induced by trauma or congenital defects such as cleft palate/lip, and a number of other musculoskeletal disorders where native bone growth is inadequate, which will be evident to those of ordinary skill in the art. The bone material can be administered to treat open fractures and fractures at high risk of non-union, and in subjects with spinal disorders, including subjects in need of spine fusion (e.g., anterior lumbar interbody fusion, posterior lumbar spinal fusion, and cervical spine fusion) or subjects having degenerative disc disease or arthritis affecting the lumbar and cervical spine.

In some embodiments, a kit for dispensing bone material into a bone implant is provided. The kit comprises a bone implant holding and shaping tray, the tray comprising a first segment having a distal end, and a first surface sized to hold and shape at least a portion of the bone implant with bone material; and the tray comprising a second segment having a second surface sized to hold and shape at least a portion of the bone implant with bone material, the second segment having a proximal end configured to be coupled to the distal end of the first segment so as to extend the first surface to hold and shape the bone implant and a spatula configured to dispense bone material from the first surface of the first segment or the second surface of the second segment into the bone implant.

In other embodiments, the kit comprises a bone implant holding and shaping tray, wherein the tray comprises a first segment having a bottom surface, and a first surface sized to hold and shape at least a portion of the bone implant with bone material; and the tray comprises a second segment having a second surface sized to hold and shape at least a portion of the bone implant with bone material, the second segment having top surface configured to be coupled to the bottom surface of the first segment so as to extend the first surface to hold and shape the bone implant and a spatula configured to dispense bone material from the first surface of the first segment or the second surface of the second segment into the bone implant.

Although the invention has been described with reference to embodiments, persons skilled in the art will recognize that changes may be made in form and detail without departing from the spirit and scope of the disclosure.

What is claimed is:

1. A bone implant holding and shaping tray, the tray comprising:
   a first segment having a distal end and a proximal end, and a first surface sized to hold and shape at least a portion of the bone implant with bone material; and
   a second segment having a second surface sized to hold and shape at least a portion of the bone implant with bone material, the second segment having a proximal end and a distal end, the proximal end of the second segment configured to be coupled to the distal end of the first segment so as to extend the first surface to hold and shape the bone implant,
   wherein the first surface comprises a plurality of parallel, elongated recesses or wells extending from the proximal end to the distal end,
   wherein the second surface comprises a plurality of parallel, elongated recesses or wells extending from the proximal end to the distal end, wherein the recesses or wells of the first and second segments are sized and configured to receive and shape said at least a portion of the bone implant with bone material, wherein (i) the distal end of the first segment is slidably coupled to the proximal end of the second segment; or (ii) the proximal end of the second segment is slidably coupled to the distal end of the first segment; or (iii) a portion of the distal end of the first segment slides within the proximal end of the first segment; or (iv) a portion of the proximal end of second segment slides within the distal end of the first segment, wherein the distal end of the first segment and the proximal end of the second segment are coupled by mating surfaces configured to lock the first segment with the second segment of the tray, wherein the tray has an expanded configuration such that the tray has a length extended from a length of the first surface to a length of the second surface and the expanded configuration comprises a maximized length of the tray, wherein the tray has a retracted configuration such that the first segment and the second segment are nested together and the first surface of the first segment covers the second surface of the second segment completely and minimizes the length of the tray.

2. The bone implant holding and shaping tray of claim 1, wherein the first segment comprises a plurality of segments, each segment configured to be slidably coupled to each other and then the second segment.

3. The bone implant holding and shaping tray of claim 1, wherein the tray comprises a third segment having a third surface sized to hold and shape at least a portion of the bone implant with bone material, the third segment having a proximal end configured to be coupled to a distal end of the second segment so as to extend the second surface to hold and shape the bone implant.

4. The bone implant holding and shaping tray of claim 1, wherein the mating surfaces comprise a snap fit fitting, an interference fitting or a tab-slot fitting.

5. The bone implant holding and shaping tray of claim 4, wherein the mating surfaces have a round, toothed, square, trapezoidal, dovetail, spiked, cantilever shape or a combination thereof.

6. The bone implant holding and shaping tray of claim 1, wherein one of the mating surfaces is located at the distal end of the first segment and the other mating surface is located at the proximal end of the second segment.

7. The bone implant holding and shaping tray of claim 6, wherein each mating surface is disposed around a perimeter of the first surface of the first segment and/or a perimeter of the second surface of the second segment.

8. The bone implant holding and shaping tray of claim 1, wherein the first surface of the first segment and the second surface of the second segment comprise a plurality of markers extending from the distal end of each segment to a region adjacent to the proximal end of each segment, each of the plurality of markers spaced a distance apart from each other such that a measured length of the finished bone implant can be determined and/or an amount of a bone material can be placed between markers for a measured dispensing of the bone material into a bone implant and/or to hold and shape the bone implant.

9. The bone implant holding and shaping tray of claim 1, wherein the first surface of the first segment or the second surface of the second segment further comprises a mixing surface comprising a bowl configured to mix and/or hold the bone material prior to dispensing of the bone material into a bone implant.

10. The bone implant holding and shaping tray of claim 1, wherein the distal end of the first surface of the first segment has an open end and the proximal end of the second surface has an open end such that the first surface and the second surface have a seamless connection when the first segment and the second segment are coupled.

\* \* \* \* \*